(12) United States Patent
Liao et al.

(10) Patent No.: US 9,498,162 B2
(45) Date of Patent: Nov. 22, 2016

(54) IDENTIFYING SEIZURES USING HEART DATA FROM TWO OR MORE WINDOWS

(75) Inventors: Wangcai Liao, Houston, TX (US); Jicong Zhang, Gainesville, FL (US)

(73) Assignee: CYBERONICS, INC., Houston, TX (US)

( * ) Notice: Subject to any disclaimer, the term of this patent is extended or adjusted under 35 U.S.C. 154(b) by 254 days.

(21) Appl. No.: 13/093,613

(22) Filed: Apr. 25, 2011

(65) Prior Publication Data

US 2012/0271182 A1 Oct. 25, 2012

(51) Int. Cl.
*A61B 5/00* (2006.01)
*A61B 5/0245* (2006.01)
*A61B 5/024* (2006.01)

(52) U.S. Cl.
CPC ........... *A61B 5/7282* (2013.01); *A61B 5/0245* (2013.01); *A61B 5/4094* (2013.01); *A61B 5/02405* (2013.01); *A61B 5/02438* (2013.01)

(58) Field of Classification Search
CPC ............ A61B 5/02405; A61B 5/0245; A61B 5/4094; A61B 5/7282
USPC .......................... 600/508–528; 607/4–28, 45
See application file for complete search history.

(56) References Cited

U.S. PATENT DOCUMENTS

| | | | |
|---|---|---|---|
| 4,172,459 A | 10/1979 | Hepp | |
| 4,291,699 A | 9/1981 | Geddes et al. | |
| 4,541,432 A | 9/1985 | Molina-Negro et al. | |
| 4,573,481 A | 3/1986 | Bullara | |
| 4,702,254 A | 10/1987 | Zabara | |
| 4,867,164 A | 9/1989 | Zabara | |
| 4,920,979 A | 5/1990 | Bullara | |
| 4,949,721 A | 8/1990 | Toriu et al. | |
| 4,979,511 A | 12/1990 | Terry, Jr. | |
| 5,025,807 A | 6/1991 | Zabara | |
| 5,113,869 A | 5/1992 | Nappholz et al. | |
| 5,137,020 A | 8/1992 | Wayne et al. | |
| 5,154,172 A | 10/1992 | Terry, Jr. et al. | |
| 5,179,950 A | 1/1993 | Stanislaw | |

(Continued)

FOREIGN PATENT DOCUMENTS

| | | |
|---|---|---|
| EP | 1145736 | 10/2001 |
| EP | 1486232 | 12/2004 |

(Continued)

OTHER PUBLICATIONS

O'Donovan, Cormac et al. "Computerized Seizures Detection Based on Heart Rate Changes", Epilepsia, vol. 36, Suppl. 4; p. 7, 1995 (1 page).

(Continued)

*Primary Examiner* — Christopher A Flory
(74) *Attorney, Agent, or Firm* — Foley & Lardner LLP

(57) ABSTRACT

Methods and systems for characterizing a seizure event in a patient, including determining a time of beat sequence of the patient's heart, determining a first HR measure for a first window, determining a second HR measure for a second window, wherein at least a portion of the first window occurs after the second window, determining at least one HR parameter based upon said first HR measure and said second HR measure, identifying an onset of the seizure event in response to determining that at least one HR parameter crosses an onset threshold, identifying an end of the seizure event in response to determining that at least one HR parameter crosses an offset threshold.

20 Claims, 9 Drawing Sheets

(56) References Cited

U.S. PATENT DOCUMENTS

| | | |
|---|---|---|
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker, Jr. et al. |
| 5,243,980 A | 9/1993 | Mehra |
| 5,251,634 A | 10/1993 | Weinberg |
| 5,263,480 A | 11/1993 | Wernicke et al. |
| 5,269,302 A | 12/1993 | Swartz et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,311,876 A | 5/1994 | Olsen et al. |
| 5,313,953 A | 5/1994 | Yomtov et al. |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,404,877 A | 4/1995 | Nolan et al. |
| 5,425,373 A | 6/1995 | Causey, III |
| 5,522,862 A | 6/1996 | Testerman et al. |
| 5,540,730 A | 7/1996 | Terry, Jr. et al. |
| 5,540,734 A | 7/1996 | Zabara |
| 5,571,150 A | 11/1996 | Wernicke et al. |
| 5,611,350 A | 3/1997 | John |
| 5,645,570 A | 7/1997 | Corbucci |
| 5,651,378 A | 7/1997 | Matheny et al. |
| 5,658,318 A | 8/1997 | Stroetmann et al. |
| 5,683,422 A | 11/1997 | Rise et al. |
| 5,690,681 A | 11/1997 | Geddes et al. |
| 5,690,688 A | 11/1997 | Noren et al. |
| 5,700,282 A | 12/1997 | Zabara |
| 5,707,400 A | 1/1998 | Terry, Jr. et al. |
| 5,716,377 A | 2/1998 | Rise et al. |
| 5,720,771 A | 2/1998 | Snell |
| 5,743,860 A | 4/1998 | Hively et al. |
| 5,792,186 A | 8/1998 | Rise |
| 5,800,474 A | 9/1998 | Benabid et al. |
| 5,833,709 A | 11/1998 | Rise et al. |
| 5,913,876 A | 6/1999 | Taylor et al. |
| 5,916,239 A | 6/1999 | Geddes et al. |
| 5,928,272 A | 7/1999 | Adkins et al. |
| 5,941,906 A | 8/1999 | Barreras, Sr. et al. |
| 5,942,979 A | 8/1999 | Luppino |
| 5,978,702 A | 11/1999 | Ward et al. |
| 5,987,352 A | 11/1999 | Klein et al. |
| 5,995,868 A | 11/1999 | Osorio et al. |
| 6,016,449 A | 1/2000 | Fischell et al. |
| 6,018,682 A | 1/2000 | Rise |
| 6,061,593 A | 5/2000 | Fischell et al. |
| 6,073,048 A | 6/2000 | Kieval et al. |
| 6,083,249 A | 7/2000 | Familoni |
| 6,091,992 A | 7/2000 | Bourgeois et al. |
| 6,104,956 A | 8/2000 | Naritoku et al. |
| 6,115,628 A | 9/2000 | Stadler et al. |
| 6,115,630 A | 9/2000 | Stadler et al. |
| 6,128,538 A | 10/2000 | Fischell et al. |
| 6,134,474 A | 10/2000 | Fischell et al. |
| 6,167,311 A | 12/2000 | Rezai |
| 6,171,239 B1 | 1/2001 | Humphrey |
| 6,175,764 B1 | 1/2001 | Loeb et al. |
| 6,205,359 B1 | 3/2001 | Boveja |
| 6,208,894 B1 | 3/2001 | Schulman et al. |
| 6,208,902 B1 | 3/2001 | Boveja |
| 6,221,908 B1 | 4/2001 | Kilgard et al. |
| 6,248,080 B1 | 6/2001 | Miesel et al. |
| 6,253,109 B1 | 6/2001 | Gielen |
| 6,269,270 B1 | 7/2001 | Boveja |
| 6,272,379 B1 | 8/2001 | Fischell et al. |
| 6,304,775 B1 | 10/2001 | Iasemidis et al. |
| 6,324,421 B1 | 11/2001 | Stadler et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,784 B1 | 3/2002 | Lozano et al. |
| 6,356,788 B2 | 3/2002 | Boveja |
| 6,366,813 B1 | 4/2002 | DiLorenzo |
| 6,366,814 B1 | 4/2002 | Boveja |
| 6,374,140 B1 | 4/2002 | Rise |
| 6,397,100 B2 | 5/2002 | Stadler et al. |
| 6,427,086 B1 | 7/2002 | Fischell et al. |
| 6,429,217 B1 | 8/2002 | Puskas |
| 6,449,512 B1 | 9/2002 | Boveja |
| 6,459,936 B2 | 10/2002 | Fischell et al. |
| 6,463,328 B1 | 10/2002 | John |
| 6,466,822 B1 | 10/2002 | Pless |
| 6,473,639 B1 | 10/2002 | Fischell et al. |
| 6,473,644 B1 | 10/2002 | Terry, Jr. et al. |
| 6,477,418 B2 | 11/2002 | Plicchi et al. |
| 6,480,743 B1 | 11/2002 | Kirkpatrick et al. |
| 6,484,132 B1 | 11/2002 | Hively et al. |
| 6,501,983 B1 | 12/2002 | Natarajan et al. |
| 6,505,074 B2 | 1/2003 | Boveja et al. |
| 6,532,388 B1 | 3/2003 | Hill et al. |
| 6,542,774 B2 | 4/2003 | Hill et al. |
| 6,549,804 B1 | 4/2003 | Osorio et al. |
| 6,556,868 B2 | 4/2003 | Naritoku et al. |
| 6,560,486 B1 | 5/2003 | Osorio et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,594,524 B2 | 7/2003 | Esteller et al. |
| 6,599,250 B2 | 7/2003 | Webb et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,985 B2 | 9/2003 | Sweeney et al. |
| 6,628,987 B1 | 9/2003 | Hill et al. |
| 6,647,296 B2 | 11/2003 | Fischell et al. |
| 6,656,125 B2 | 12/2003 | Misczynski et al. |
| 6,656,960 B2 | 12/2003 | Puskas |
| 6,668,191 B1 | 12/2003 | Boveja |
| 6,671,555 B2 | 12/2003 | Gielen et al. |
| 6,671,556 B2 | 12/2003 | Osorio et al. |
| 6,684,105 B2 | 1/2004 | Cohen et al. |
| 6,721,603 B2 | 4/2004 | Zabara et al. |
| 6,735,474 B1 | 5/2004 | Loeb et al. |
| 6,738,671 B2 | 5/2004 | Christophersom et al. |
| 6,760,626 B1 | 7/2004 | Boveja |
| 6,768,969 B1 | 7/2004 | Nikitin et al. |
| 6,788,975 B1 | 9/2004 | Whitehurst et al. |
| 6,793,670 B2 | 9/2004 | Osorio et al. |
| 6,819,953 B2 | 11/2004 | Yonce et al. |
| 6,819,956 B2 | 11/2004 | DiLorenzo |
| 6,832,114 B1 | 12/2004 | Whitehurst et al. |
| 6,836,685 B1 | 12/2004 | Fitz |
| 6,885,888 B2 | 4/2005 | Rezai |
| 6,904,390 B2 | 6/2005 | Nikitin et al. |
| 6,920,357 B2 | 7/2005 | Osorio et al. |
| 6,934,580 B1 | 8/2005 | Osorio et al. |
| 6,934,585 B1 | 8/2005 | Schloss |
| 6,944,501 B1 | 9/2005 | Pless |
| 6,957,107 B2 | 10/2005 | Rogers |
| 6,961,618 B2 | 11/2005 | Osorio et al. |
| 6,985,771 B2 | 1/2006 | Fischell et al. |
| 6,990,377 B2 | 1/2006 | Gliner et al. |
| 7,006,859 B2 | 2/2006 | Osorio et al. |
| 7,006,872 B2 | 2/2006 | Gielen et al. |
| 7,010,351 B2 | 3/2006 | Firlik et al. |
| 7,024,247 B2 | 4/2006 | Gliner et al. |
| 7,054,792 B2 | 5/2006 | Frei et al. |
| 7,058,453 B2 | 6/2006 | Nelson et al. |
| 7,076,288 B2 | 7/2006 | Skinner |
| 7,079,977 B2 | 7/2006 | Osorio et al. |

(56) References Cited

U.S. PATENT DOCUMENTS

| | | |
|---|---|---|
| 7,134,996 B2 | 11/2006 | Bardy |
| 7,139,677 B2 | 11/2006 | Hively et al. |
| 7,146,211 B2 | 12/2006 | Frei et al. |
| 7,146,217 B2 | 12/2006 | Firlik et al. |
| 7,146,218 B2 | 12/2006 | Esteller et al. |
| 7,149,572 B2 | 12/2006 | Frei et al. |
| 7,164,941 B2 | 1/2007 | Misczynski et al. |
| 7,167,750 B2 | 1/2007 | Knudson et al. |
| 7,174,206 B2 | 2/2007 | Frei et al. |
| 7,177,678 B1 | 2/2007 | Osorio et al. |
| 7,188,053 B2 | 3/2007 | Nikitin et al. |
| 7,204,833 B1 | 4/2007 | Osorio et al. |
| 7,209,786 B2 | 4/2007 | Brockway |
| 7,209,787 B2 | 4/2007 | DiLorenzo |
| 7,221,981 B2 | 5/2007 | Gliner |
| 7,228,167 B2 | 6/2007 | Kara |
| 7,231,254 B2 | 6/2007 | DiLorenzo |
| 7,236,830 B2 | 6/2007 | Gliner |
| 7,236,831 B2 | 6/2007 | Firlik et al. |
| 7,242,983 B2 | 7/2007 | Frei et al. |
| 7,242,984 B2 | 7/2007 | DiLorenzo |
| 7,254,439 B2 | 8/2007 | Misczynski et al. |
| 7,263,467 B2 | 8/2007 | Sackellares et al. |
| 7,277,758 B2 | 10/2007 | DiLorenzo |
| 7,280,867 B2 | 10/2007 | Frei et al. |
| 7,282,030 B2 | 10/2007 | Frei et al. |
| 7,289,844 B2 | 10/2007 | Misczynski et al. |
| 7,292,890 B2 | 11/2007 | Whitehurst et al. |
| 7,295,881 B2 | 11/2007 | Cohen et al. |
| 7,299,096 B2 | 11/2007 | Balzer et al. |
| 7,302,298 B2 | 11/2007 | Lowry et al. |
| 7,305,268 B2 | 12/2007 | Gliner et al. |
| 7,314,451 B2 * | 1/2008 | Halperin et al. ............... 600/534 |
| 7,321,837 B2 | 1/2008 | Osorio et al. |
| 7,324,850 B2 | 1/2008 | Persen et al. |
| 7,324,851 B1 | 1/2008 | DiLorenzo |
| 7,346,391 B1 | 3/2008 | Osorio et al. |
| 7,353,063 B2 | 4/2008 | Simms, Jr. |
| 7,353,064 B2 | 4/2008 | Gliner et al. |
| 7,373,199 B2 | 5/2008 | Sackellares et al. |
| 7,389,144 B1 | 6/2008 | Osorio et al. |
| 7,401,008 B2 | 7/2008 | Frei et al. |
| 7,403,820 B2 | 7/2008 | DiLorenzo |
| 7,433,732 B1 | 10/2008 | Carney et al. |
| 7,657,307 B2 * | 2/2010 | Van Dam et al. ............ 600/515 |
| 8,562,536 B2 * | 10/2013 | Osorio et al. ................ 600/483 |
| 8,827,912 B2 * | 9/2014 | Bukhman ..................... 600/483 |
| 9,050,469 B1 * | 6/2015 | Osorio et al. |
| 9,241,647 B2 * | 1/2016 | Osorio ............... A61B 5/02405 |
| 2002/0072782 A1 | 6/2002 | Osorio et al. |
| 2002/0099417 A1 | 7/2002 | Naritoku et al. |
| 2002/0116030 A1 | 8/2002 | Rezai |
| 2002/0151939 A1 | 10/2002 | Rezai |
| 2002/0188214 A1 | 12/2002 | Misczynski et al. |
| 2003/0074032 A1 | 4/2003 | Gliner |
| 2003/0083716 A1 | 5/2003 | Nicolelis et al. |
| 2003/0083726 A1 | 5/2003 | Zeijlemaker et al. |
| 2003/0125786 A1 | 7/2003 | Gliner et al. |
| 2003/0130706 A1 | 7/2003 | Sheffield et al. |
| 2003/0144829 A1 | 7/2003 | Geatz et al. |
| 2003/0181954 A1 | 9/2003 | Rezai |
| 2003/0181958 A1 | 9/2003 | Dobak |
| 2003/0208212 A1 | 11/2003 | Cigaina |
| 2003/0210147 A1 | 11/2003 | Humbard |
| 2003/0212440 A1 | 11/2003 | Boveja |
| 2003/0236558 A1 | 12/2003 | Whitehurst et al. |
| 2004/0006278 A1 | 1/2004 | Webb et al. |
| 2004/0088024 A1 | 5/2004 | Firlik et al. |
| 2004/0122484 A1 | 6/2004 | Hatlestad et al. |
| 2004/0122485 A1 | 6/2004 | Stahmann et al. |
| 2004/0133119 A1 | 7/2004 | Osorio et al. |
| 2004/0138516 A1 | 7/2004 | Osorio et al. |
| 2004/0138517 A1 | 7/2004 | Osorio et al. |
| 2004/0138647 A1 | 7/2004 | Osorio et al. |
| 2004/0138711 A1 | 7/2004 | Osorio et al. |
| 2004/0153129 A1 | 8/2004 | Pless et al. |
| 2004/0158119 A1 | 8/2004 | Osorio et al. |
| 2004/0158165 A1 | 8/2004 | Yonce et al. |
| 2004/0172085 A1 | 9/2004 | Knudson et al. |
| 2004/0172091 A1 | 9/2004 | Rezai |
| 2004/0172094 A1 | 9/2004 | Cohen et al. |
| 2004/0176812 A1 | 9/2004 | Knudson et al. |
| 2004/0176831 A1 | 9/2004 | Gliner et al. |
| 2004/0199212 A1 | 10/2004 | Fischell et al. |
| 2004/0249302 A1 | 12/2004 | Donoghue et al. |
| 2004/0249416 A1 | 12/2004 | Yun et al. |
| 2005/0004621 A1 | 1/2005 | Boveja et al. |
| 2005/0020887 A1 | 1/2005 | Goldberg |
| 2005/0021092 A1 | 1/2005 | Yun et al. |
| 2005/0021103 A1 | 1/2005 | DiLorenzo |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0027284 A1 | 2/2005 | Lozano et al. |
| 2005/0033378 A1 | 2/2005 | Sheffield et al. |
| 2005/0033379 A1 | 2/2005 | Lozano et al. |
| 2005/0038484 A1 | 2/2005 | Knudson et al. |
| 2005/0049515 A1 | 3/2005 | Misczynski et al. |
| 2005/0049655 A1 | 3/2005 | Boveja et al. |
| 2005/0065562 A1 | 3/2005 | Rezai |
| 2005/0065573 A1 | 3/2005 | Rezai |
| 2005/0065574 A1 | 3/2005 | Rezai |
| 2005/0065575 A1 | 3/2005 | Dobak |
| 2005/0070971 A1 | 3/2005 | Fowler et al. |
| 2005/0075701 A1 | 4/2005 | Shafer |
| 2005/0075702 A1 | 4/2005 | Shafer |
| 2005/0101873 A1 | 5/2005 | Misczynski et al. |
| 2005/0119703 A1 | 6/2005 | DiLorenzo |
| 2005/0124901 A1 | 6/2005 | Misczynski et al. |
| 2005/0131467 A1 | 6/2005 | Boveja et al. |
| 2005/0131485 A1 | 6/2005 | Knudson et al. |
| 2005/0131486 A1 | 6/2005 | Boveja et al. |
| 2005/0131493 A1 | 6/2005 | Boveja et al. |
| 2005/0143786 A1 | 6/2005 | Boveja et al. |
| 2005/0148893 A1 | 7/2005 | Misczynski et al. |
| 2005/0148894 A1 | 7/2005 | Misczynski et al. |
| 2005/0148895 A1 | 7/2005 | Misczynski et al. |
| 2005/0153885 A1 | 7/2005 | Yun et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0187590 A1 | 8/2005 | Boveja et al. |
| 2005/0192644 A1 | 9/2005 | Boveja et al. |
| 2005/0197590 A1 | 9/2005 | Osorio et al. |
| 2005/0245971 A1 | 11/2005 | Brockway et al. |
| 2005/0261542 A1 | 11/2005 | Riehl |
| 2005/0277998 A1 | 12/2005 | Tracey et al. |
| 2005/0283200 A1 | 12/2005 | Rezai et al. |
| 2005/0283201 A1 | 12/2005 | Machado et al. |
| 2005/0288600 A1 | 12/2005 | Zhang et al. |
| 2005/0288760 A1 | 12/2005 | Machado et al. |
| 2006/0009815 A1 | 1/2006 | Boveja |
| 2006/0058851 A1 * | 3/2006 | Cigaina ............... A61B 5/02405 607/40 |
| 2006/0074450 A1 | 4/2006 | Boveja |
| 2006/0079936 A1 | 4/2006 | Boveja |
| 2006/0094971 A1 | 5/2006 | Drew |
| 2006/0095081 A1 | 5/2006 | Zhou et al. |
| 2006/0106430 A1 | 5/2006 | Fowler et al. |
| 2006/0135877 A1 | 6/2006 | Giftakis et al. |
| 2006/0135881 A1 | 6/2006 | Giftakis et al. |
| 2006/0155495 A1 | 7/2006 | Osorio et al. |
| 2006/0167497 A1 | 7/2006 | Armstrong et al. |
| 2006/0173493 A1 | 8/2006 | Armstrong et al. |
| 2006/0173522 A1 | 8/2006 | Osorio |
| 2006/0190056 A1 | 8/2006 | Fowler et al. |
| 2006/0195163 A1 | 8/2006 | KenKnight et al. |
| 2006/0200206 A1 | 9/2006 | Firlik et al. |
| 2006/0212091 A1 | 9/2006 | Lozano et al. |
| 2006/0224067 A1 | 10/2006 | Giftakis et al. |
| 2006/0224191 A1 | 10/2006 | DiLorenzo |
| 2006/0241697 A1 | 10/2006 | Libbus et al. |

(56) References Cited

U.S. PATENT DOCUMENTS

| | | |
|---|---|---|
| 2006/0241725 A1 | 10/2006 | Libbus et al. |
| 2006/0293720 A1 | 12/2006 | DiLorenzo |
| 2007/0027486 A1 | 2/2007 | Armstrong et al. |
| 2007/0027497 A1 | 2/2007 | Parnis et al. |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand et al. |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0238939 A1 | 10/2007 | Giftakis et al. |
| 2007/0239210 A1 | 10/2007 | Libbus et al. |
| 2007/0239230 A1* | 10/2007 | Giftakis et al. ............... 607/62 |
| 2007/0244407 A1 | 10/2007 | Osorio |
| 2007/0249953 A1 | 10/2007 | Osorio et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260286 A1* | 11/2007 | Giftakis et al. ............... 607/9 |
| 2007/0260289 A1 | 11/2007 | Giftakis et al. |
| 2007/0265536 A1 | 11/2007 | Giftakis et al. |
| 2007/0265677 A1* | 11/2007 | Giftakis et al. ............... 607/45 |
| 2007/0272260 A1 | 11/2007 | Nikitin et al. |
| 2007/0282177 A1 | 12/2007 | Pilz |
| 2008/0033490 A1* | 2/2008 | Giftakis et al. ............... 607/2 |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |
| 2008/0319281 A1* | 12/2008 | Aarts ............................. 600/301 |
| 2010/0274303 A1* | 10/2010 | Bukhman ....................... 607/3 |
| 2011/0270346 A1* | 11/2011 | Frei .................. A61B 5/0245 607/45 |
| 2011/0270347 A1* | 11/2011 | Frei .................. A61B 5/02405 607/45 |
| 2012/0071774 A1* | 3/2012 | Osorio et al. ................ 600/512 |
| 2014/0378851 A1* | 12/2014 | Frei .................. A61B 5/02405 600/508 |
| 2016/0081610 A1* | 3/2016 | Osorio .............. A61B 5/02405 600/508 |

FOREIGN PATENT DOCUMENTS

| | | |
|---|---|---|
| EP | 2258444 A1 | 12/2010 |
| GB | 2026870 | 2/1980 |
| GB | 2079610 | 1/1982 |
| WO | 00/64336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2007143234 A2 | 12/2007 |
| WO | 2008/045597 | 4/2008 |

OTHER PUBLICATIONS

Robinson, Stephen E. et al. "Heart Rate Variability Changes as Predictor of Response to Vagal Nerve Stimulation Therapy for Epilepsy", Epilepsia, vol. 40, Suppl. 7, p. 147; 1999 (1 page).

Long, Teresa J. et al. "Effectiveness of Heart Rate Seizures Detection Compared to EEG in an Epilepsy Monitoring Unit (EMU)", Epilepsia, vol. 40, Suppl. 7, p. 174; 1999 (1 page).

Dimkpa, Uchechukwu "Post-Exercise Heart Rate Recovery; An Index of Cardiovascular Fitness", Official Research Journal of the American Society of Exercise Physiologists (ASEP), vol. 12, No. 1, pp. 10-23, Feb. 2009 (14 pages).

Hautala, Arto J. et al. "Heart Rate Recovery After Maximal Exercise is Associated with Acetylcholine Receptor M2 (CHRM2) Gene Polymorphism", American Journal Physiological Society, Circ Physiol 291, pp. H459-H466, Feb. 26, 2006 (8 pages).

Nishime, Erna Obenza et al. "Heart Rate Recovery and Treadmill Exercise Score as Predictors of Mortality in Patients Referred for Exercise ECG", Journal of American Medical Association, vol. 284, No. 11, pp. 1392-1398, Sep. 20, 2000 (7 pages).

Du, Na et al. "Heart Rate Recovery After Exercise and Neural Regulation of Heart Rate Variability in 30-40 Year Old Female Marathon Runners", Journal of Sports and Medicine, pp. 9-17, 2005, (9 pages).

PCT Search Report and Written Opinion for International Application No. PCT/US2012/020329, dated May 18, 2012, 13 pages.

Bachman, D.,S. et al.; *"Effects of Vagal Volleys and Serotonin on Units of Cingulate Cortex in Monkeys;"* Brain Research, vol. 130 (1977). pp. 253-269.

Baevskii, R.M. *"Analysis of Heart Rate Variability in Space Medicine;"* Human Physiology, vol. 28, No. 2, (2002); pp. 202-213.

Baevsky, R.M., et al.; *"Autonomic Cardiovascular and Respiratory Control During Prolonged Spaceflights Aboard the International Space Station;"* J. Applied Physiological, vol. 103, (2007) pp. 156-161.

Boon, P., et al.; *"Vagus Nerve Stimulation for Epilepsy, Clinical Efficacy of Programmed and Magnet Stimulation;"* (2001); pp. 93-98.

Boon, Paul, et al.; *"Programmed and Magnet-Induced Vagus Nerve Stimulation for Refractory Epilepsy;"* Journal of Clinical Neurophysiology vol. 18 No. 5; (2001); pp. 402-407.

Borovikova, L.V., et al.; *"Vagus Nerve Stimulation Attenuates the Systemic Inflammatory Response to Endotoxin;"* Letters to Nature; vol. 405; (May 2000); pp. 458-462.

Brack, Kieran E., et al.; *"Interaction Between Direct Sympathetic and Vagus Nerve Stimulation on Heart Rate in the Isolated Rabbit Heart;"* Experimental Physiology vol. 89, No. 1; pp. 128-139.

(56) References Cited

OTHER PUBLICATIONS

Chakravarthy, N., et al.; "*Controlling Synchronization in a Neuron-Level Population Model;*" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat;*" Neurobiology of Learning and Memory, vol. 70, 364-373 (1998).

Elmpt, W.J.C., et al.; "*A Model of Heart Rate Changes to Detect Seizures in Severe Epilepsy*" Seizure vol. 15, (2006) pp. 366-375.

Frei, M.G., et al.; "*Left Vagus Nerve Stimulation with the Neurocybernetic Prosthesis Has Complex Effects on Heart Rate and on Its Variability in Humans:*" Epilepsia, vol. 42, No. 8 (2001); pp. 1007-1016.

George, M.S., et al.; "*Vagus Nerve Stimulation: A New Tool for Brain Research and Therapy;*" Society of Biological Psychiatry vol. 47 (2000) pp. 287-295.

"*Heart Rate Variability—Standards of Measurement, Physiological Interpretation, and Clinical Use*" Circulation—Electrophysiology vol. 93, No. 5; http://circ.ahajournals.org/cgi/content-nw/full/93/5/1043/F3.

Henry, Thomas R.; "*Therapeutic Mechanisms of Vague Name Stimulation;*". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys;*" Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques;*" IEEE Transactions on Biomedical Engineering, vol. 51, No. 3 (Mar. 2004); pp. 493-506.

Iasemidis; L.D., et al.; "*Spatiotemporal Transition to Epileptic Seizures: A Nonlinear Dynamical Analysis of Scalp and Intracranial EEG Recordings;*" Spatiotemporal Models in Biological and Artificial Systems; F.L. Silva et al. (Eds.) IOS Press, 1997; pp. 81-88.

Iasemidis, L.D.; "Epileptic *Seizure Prediction and Control*" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*" Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press—YSEIZ-1305; pp. 1-4.

Koo, B., "*EEG Changes With Vagus Nerve Stimulation*" Journal of Clinical Neurophysiology, vol. 18 No. 5 (Sep. 2001); pp. 434-441.

Krittayaphong, M.D., et al.; "*Heart Rate Variability in Patients with Coronary Artery Disease: Differences in Patients with Higher and Lower Depression Scores*" Psychosomatic Medicine vol. 59 (1997) pp. 231-235.

Leutmezer, F., et al.; "*Electrocardiographic Changes at the Onset of Epileptic Seizures;*" Epilepsia, vol. 44, No. 3; (2003); pp. 348-354.

Lewis, M.E., et al.; "Vagus Nerve Stimulation Decreases Left Ventricular Contractility in Vivo in the Human and Pig Heart" *The Journal of Physiology* vol. 534, No. 2, (2001) pp. 547-552.

Li, M., et al.; "*Vagal Nerve Stimulation Markedly Improves Long-Term Survival After Chronic Heart Failure in Rats:*" Circulation (Jan. 2004) pp. 120-124.

Licht, C.M.M.; *Association Between Major Depressive Disorder and Heart Rate Variability in the Netherlands Study of Depression and Anxiety* (*NESDA*); Arch. Gen Psychiatry, vol. 65, No. 12 (Dec. 2008); pp. 1358-1367.

Lockard et al., "*Feasibility and Safety of Vagal Stimulation in Monkey Model;*" Epilepsia, vol. 31 (Supp. 2) (1990), pp. S20-S26.

McClintock, P., "*Can Noise Actually Boost Brain Power*" Physics World Jul. 2002; pp. 20-21.

Mori, T., et al.; "*Noise-Induced Entrainment and Stochastic Resonance in Human Brain Waves*" Physical Review Letters vol. 88, No. 21 (2002); pp. 218101-1-218101-4.

Mormann, F., "Seizure prediction: the long and winding road," Brain 130 (2007), 314-333.

Nouri, M.D.; "*Epilepsy and the Autonomic Nervous System*" emedicine (updated May 5, 2006); pp. 1-14; http://www.emedicine.com/neuro/topic658.htm.

O'Regan, M.E., et al.; "*Abnormalities in Cardiac and Respiratory Function Observed During Seizures in Childhood*" Developmental Medicine & Child Neurology, vol. 47 (2005) pp. 4-9.

Pathwardhan, R.V., et al., Control of Refractory status epilepticus precipitated by anticonvulasnt withdrawal using left vagal nerve stimulation: a case report, Surgical Neurology 64 (2005) 170-73.

Poddubnaya, E.P., "Complex Estimation of Adaptation Abilities of the Organism in Children Using the Indices of Responsiveness of the Cardiovascular System and Characteristics of EEG" *Neurophysiology* vol. 38, No. 1 (2006); pp. 63-74.

Rugg-Gunn, F.J., et al.; "*Cardiac Arrhythmias in Focal Epilepsy: a Prospective Long-Term Study*" www.thelancet.com vol. 364 (2004) pp. 2212-2219.

Sajadieh, A., et al.; "*Increased Heart Rate and Reduced Heart-Rte Variability are Associated with Subclinical Inflammation in Middle-Aged and Elderly Subjects with No Apparent Heart Disease*" European Heart Journal vol. 25, (2004); pp. 363-370.

Schernthaner, C., et al.; "*Autonomic Epilepsy—The Influence of Epileptic Discharges on Heart Rate and Rhythm*"The Middle European Journal of Medicine vol. 111, No. 10 (1999) pp. 392-401.

Terry et al.; "*The Implantable Neurocybernetic Prosthesis System*", Pacing and Clinical Electrophysiology, vol. 14, No. 1 (Jan. 1991), pp. 86-93.

Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.

Umetani, M.D., et al.; "*Twenty-Four Hour Time Domain Heart Rate Variability and Heart Rate: Relations to Age and Gender Over Nince Decades*"JACC vol. 31, No. 3; (Mar. 1998); pp. 593-601.

Vonck, K., et al. "*The Mechanism of Action of Vagus Nerve Stimulation for Refractory Epilepsy—The Current Status*", Journal of Neurophysiology, vol. 18 No. 5 (2001), pp. 394-401.

Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.

Zabara, J.; "*Neuroinhibition of Xylaine Induced Emesis*" Pharmacology & Toxicology, vol. 63 (1988) pp. 70-74.

Zabara, J. "*Inhibition of Experimental Seizures in Canines by Repetivie Vagal Stimulation*" Epilepsia vol. 33, No. 6 (1992); pp. 1005-1012.

Zabara, J., et al.; "*Neural Control of Circulation I*"The Physiologist, vol. 28 No. 4 (1985); 1 page.

Zabara, J., et al.; "*Neuroinhibition in the Regulation of Emesis*" Space Life Sciences, vol. 3 (1972) pp. 282-292.

Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.

Osorio, Ivan et al., "Automated Seizure Abatement in Humans Using Electrical Stimulation," Annals of Neurology, vol. 57, No. 2, pp. 258-268, 2005.

Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.

Weil, Sabine et al, "Heart Rate Increase in Otherwise Subclinical Seizures Is Different in Temporal Versus Extratemporal Seizure Onset: Support for Temporal Lobe Automatic Influence," Epileptic Disord., vol. 7, No. 3, Sep. 2005, pp. 199-204.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

(56) References Cited

OTHER PUBLICATIONS

Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

O'Donovan, Cormac A. et al., "Computerized Seizure Detection Based on Heart Rate Changes," abstract of AES Proceedings, Epilepsia, vol. 36, Suppl. 4, 1995, p. 7.

Robinson, Stephen E et al., "Heart Rate Variability Changes As Predictor of Response to Vagal Nerve Stimulation Therapy for Epilepsy," abstract of AES Proceedings,Epilepsia, vol. 40, Suppl. 7, 1999, p. 147.

Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.

\* cited by examiner

IDENTIFYING SEIZURES USING HEART DATA FROM TWO OR MORE WINDOWS

A. CROSS-REFERENCE TO RELATED APPLICATIONS

This application relates to the following commonly assigned co-pending application entitled:

"Identifying Seizures Using Heart Rate Decrease," Ser. No. 13/093,475, filed Apr. 25, 2011.

B. BACKGROUND

1. Technical Field of the Present Disclosure

The present disclosure relates generally to the field of seizure identification and more particularly to the field of identifying seizures by monitoring and comparing heart data from two or more windows.

2. Background of the Present Disclosure

Seizures generally are characterized by abnormal/excessive neural activity in the brain. Seizures may involve loss of consciousness or awareness, and cause falls, uncontrollable convulsions, etc. Significant injuries may result not only from the neuronal activity in the brain but also from the associated loss of motor function from falls or the inability to perceive and/or respond appropriately to potential danger or harm.

It is important to identify seizures as quickly as possible after the onset of the seizure to allow corrective action to be taken immediately, including administering therapy or intervening to prevent injury to the patient. It is also important to be able to identify and record seizures that have occurred to accurately assess the state of the patient's condition and determine whether therapies are effective or should be modified. Seizure detection algorithms have been proposed using a variety of body parameters to detect seizures, including brain waves (e.g., electroencephalogram or EEG signals), heart beats (e.g., electrocardiogram or EKG signals), and movements (e.g., triaxial accelerometer signals). See, e.g., U.S. Pat. No. 5,928,272, and U.S. application Ser. No. 12/770,562, both of which are hereby incorporated by reference herein.

Detection of seizures using heart data requires that the algorithm distinguish between pathological changes in the detected heart signal (which indicate a seizure) and non-pathological changes that may be similar to pathological changes but involve normal physiological functioning. For example, the heart rate may rise both when a seizure event occurs and when the patient exercises, climbs stairs or performs other physiologically demanding acts.

Seizure detection algorithms, in some instances, may need to distinguish between changes in heart rate due to a seizure and those due to exertional or positional/postural changes. As noted, it is important to detect seizures quickly and accurately. However, current algorithms fail to provide rapid and accurate detection. Current algorithms also fail to provide an indication of when the seizure has ended and the danger to the patient is reduced. The present invention addresses limitations associated with existing cardiac-based seizure detection algorithms.

C. SUMMARY

In one respect, disclosed is a method for characterizing a seizure event in a patient, the method comprising determining a time of beat sequence of the patient's heart, determining a first HR measure for a first window, determining a second HR measure for a second window, wherein at least a portion of the first window occurs after the second window, determining at least one HR parameter based upon said first HR measure and said second HR measure, identifying the onset of a seizure event in response to determining that at least one HR parameter crosses an onset threshold, and identifying an end of the seizure event in response to determining that at least one HR parameter crosses an offset threshold.

In another respect, disclosed is a system for characterizing seizure events, the system comprising one or more processors, one or more memory units coupled to the one or more processors, the system being configured to determine a time of beat sequence of the patient's heart, determine a first HR measure for a first window, determine a second HR measure for a second window, wherein at least a portion of the first window occurs after the second window, determine at least one HR parameter based upon said first HR measure and said second HR measure, identify the onset of a seizure event in response to determining that at least one HR parameter crosses an onset threshold, and identify an end of the seizure event in response to determining that at least one HR parameter crosses is an offset threshold.

In yet another respect, disclosed is a computer program product embodied in a computer-operable medium, the computer program product comprising logic instructions, the logic instructions being effective to determine a first HR measure for a first window in a time series of heart beat data for a patient, determine a second HR measure for a second window, wherein at least a portion of the first window occurs after the second window, determining at least one HR parameter based upon said first HR measure and said second HR measure, identify the onset of a seizure event in response to determining that at least one HR parameter crosses an onset threshold, and identify an end of the seizure event in response to determining that at least one HR parameter crosses an offset threshold.

In some respects, disclosed is a method for characterizing a seizure event in a patient, the method comprising determining heart rate (HR) versus time, determining a first HR measure for a first window, determining a second HR measure for a second window, wherein at least a portion of the first window occurs after the second window, and wherein the first window and the second window are separated by an intermediate window, determining at least one HR parameter based upon said first HR measure and said second HR measure, and identifying an onset of the seizure event in response to determining that at least one HR parameter crosses an onset threshold.

In some respects, disclosed is a system for characterizing a seizure event in a patient, the system comprising one or more processors, one or more memory units coupled to the one or more processors, the system being configured to determine heart rate (HR) versus time, determine a first HR measure for a first window, determine a second HR measure for a second window, wherein at least a portion of the first window occurs after the second window, and wherein the first window and the second window are separated by an intermediate window, determine at least one HR parameter based upon said first HR measure and said second HR measure, and identify an onset of the seizure event in response to determining that at least one HR parameter crosses an onset threshold.

In some respects, disclosed is a computer program product embodied in a computer-operable medium, the computer program product comprising logic instructions, the logic instructions being effective to determine heart rate (HR)

versus time, determine a first HR measure for a first window, determine a second HR measure for a second window, wherein at least a portion of the first window occurs after the second window, and wherein the first window and the second window are separated by an intermediate window, determine at least one HR parameter based upon said first HR measure and said second HR measure, and identify an onset of the seizure event in response to determining that at least one HR parameter crosses an onset threshold.

Numerous additional embodiments are also possible.

One particular advantage provided by at least one of the disclosed embodiments is a seizure detection algorithm that identifies both the start (or onset) of a seizure and the end of the seizure. An additional advantage provided by at least one of the disclosed embodiments is an algorithm with improved accuracy in detecting seizures.

D. BRIEF DESCRIPTION OF THE DRAWINGS

Other objects and advantages of the present disclosure may become apparent upon reading the detailed description and upon reference to the accompanying drawings.

Figure 1:
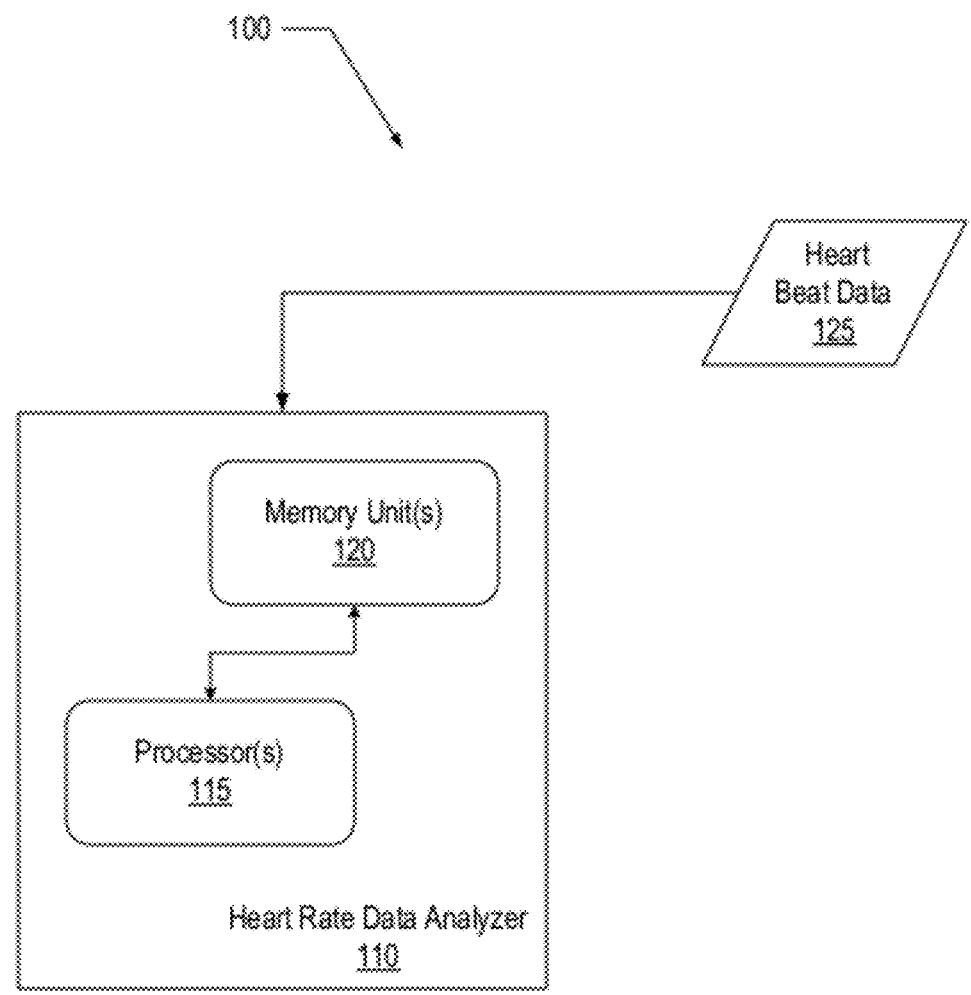
FIG. 1 is a block diagram illustrating a system for identifying a seizure using heart beat data, in accordance with some embodiments.

While the present disclosure is subject to various modifications and alternative forms, specific embodiments of the claimed subject matter are shown by way of example in the drawings and the accompanying detailed description. The drawings and detailed description are not intended to limit the present claimed subject matter to the particular embodiments. This disclosure is instead intended to cover all modifications, equivalents, and alternatives falling within the scope of the present claimed subject matter.

E. DETAILED DESCRIPTION

One or more embodiments of the present claimed subject matter are described below. It should be noted that these and any other embodiments are exemplary and are intended to be illustrative of the claimed subject matter rather than limiting. While the present claimed subject matter is widely applicable to different types of systems, it is impossible to include all of the possible embodiments and contexts of the present claimed subject matter in this disclosure. Upon reading this disclosure, many alternative embodiments of the present claimed subject matter will be apparent to persons of ordinary skill in the art.

The various illustrative logical blocks, modules, circuits, and algorithm steps described in connection with the embodiments disclosed here may be implemented as electronic/computer hardware, computer software, or combinations of the two. Various illustrative components, blocks, modules, circuits, and steps are described generally in terms of their functionality. Whether such functionality is implemented as hardware or software may depend upon the particular application and imposed design constraints. The described functionality may be implemented in varying ways for each particular application, but such implementation decisions should not be interpreted as causing a departure from the scope of the present claimed subject matter.

In general, a seizure may cause an increase in a subject's heart rate (HR) during the onset of the seizure and a corresponding decrease in HR during/after the offset of a seizure. Typically, the HR may be at a resting HR before the seizure, may increase at the beginning of a seizure, rise to a certain peak HR during the seizure, and then decrease back to a resting HR after the seizure has ended. This series of HR changes associated with the seizure may be used in the seizure identification process.

Referring to FIG. 1, a particular illustrative embodiment of a block diagram illustrating a system for identifying a seizure using heart rate data is shown and generally designated 100. System 100 may include a heart rate data analyzer 110, which is configured to receive and analyze heart beat data 125. Heart beat data 125 may be a series of heart beats at given points in time. The heart beat data may be received in real time or near real time from a subject or the heart beat data may be data that was previously recorded and is being received from a storage device. In some embodiments, heart rate may be computed from the received heart beat data. In alternative embodiments, heart rate data may be received directly instead of or in addition to the heart beat data.

In some embodiments, heart rate data analyzer 110 may be configured to analyze the heart beat data 125 and identify seizure events that the subject may have suffered and/or is currently suffering. Heart rate data analyzer 110 may be configured to monitor the heart rate within a certain window. In some embodiments, the window may comprise two or more windows of heart rate data or heart beat data 125. In some embodiments, a seizure onset (or seizure beginning) and a seizure end may be identified by comparing statistical measures of heart rate values in the windows.

The functionality of heart rate data analyzer 110 may be implemented using one or more processors such as processor(s) 115 and one or more memory units coupled to the one or more processors such as memory unit(s) 120. The system 100 may be configured to determine heart rate (HR) versus time, to determine a first HR measure for a first window, and to determine a second HR measure for a second window, where at least a portion of the first window occurs after the second window. "HR measure" may refer to an instantaneous HR or may refer to a statistical measure of central tendency (e.g., a median or an average/mean) in a window (e.g., a time window or a number-of-beats window). Parameters such as HRV measures, or differences and/or ratios of short and long windows may be used to provide meaningful indications of changes in the cardiac status of a patient.

The system 100 may be further configured to determine at least one HR parameter based upon said first HR measure and said second HR measure, to identify an onset of the seizure event in response to determining that at least one HR parameter crosses an onset threshold, and to identify an end of the seizure event in response to determining that at least one HR parameter crosses an offset threshold.

Additionally, the first window and the second window may be separated by an intermediate window. The first window, the intermediate window, and the second window may be windows in either a time domain or a heart beat domain.

Additionally, the first HR measure may be a first median HR in the first window, the second HR measure may be a second median HR in the second window, at least one HR parameter may be a ratio of the first median HR to the second median HR, the at least one HR parameter crossing the onset threshold may comprise the HR parameter being greater than the onset threshold. In one embodiment, the onset threshold may be 1.25, and the offset threshold may be a number less than 1.0, for example about 0.9.

Additionally, the at least one HR parameter crossing the offset threshold may comprise the HR parameter being less than the offset threshold.

Figure 2:
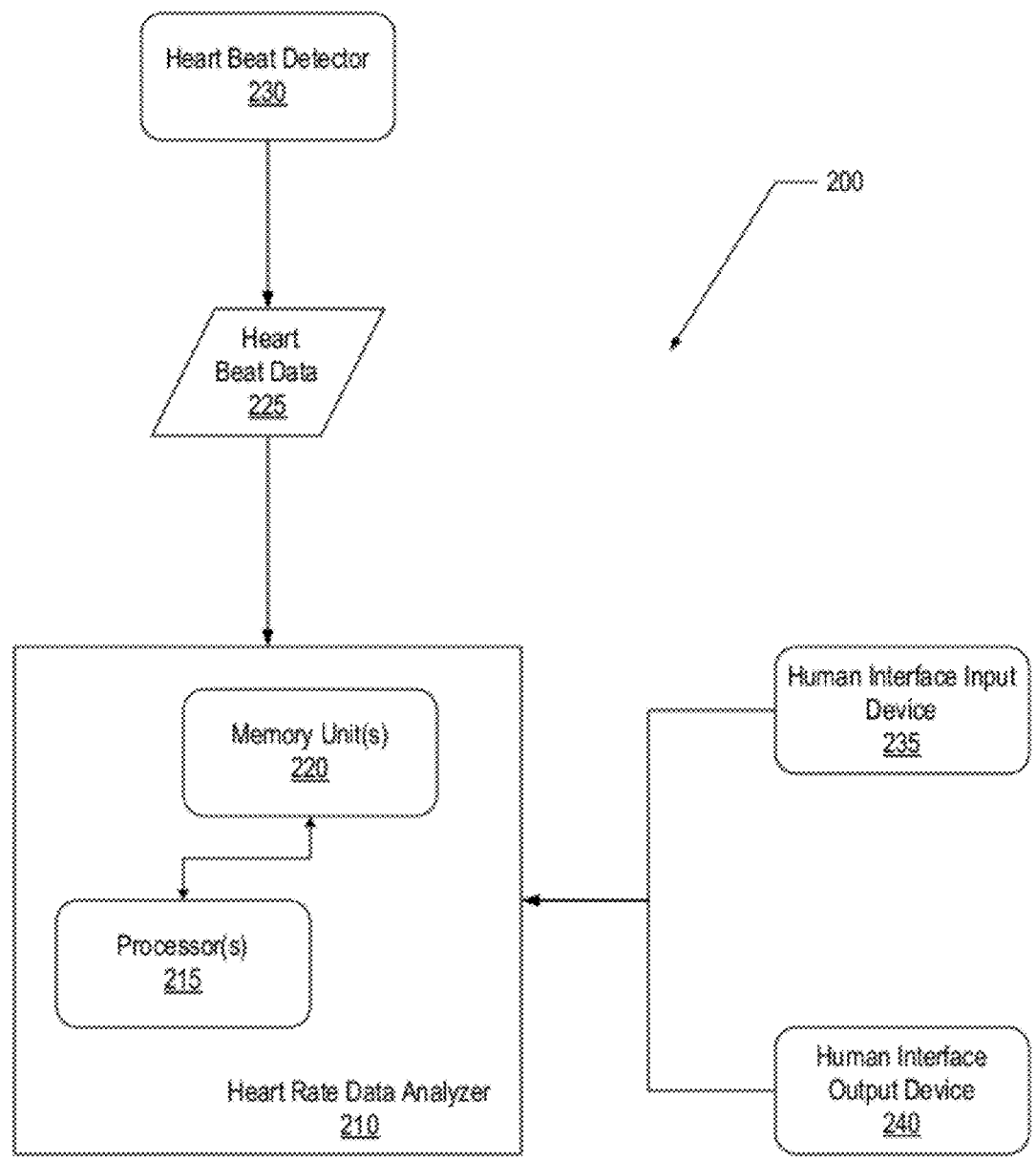
FIG. 2 is a block diagram illustrating an alternative system for identifying a seizure using heart beat data, in accordance with some embodiments.

Referring to FIG. 2, a block diagram is provided showing one example of an embodiment of a system for identifying a seizure using heart beat data.

The system, generally designated 200, may include a heart rate data analyzer 210, a heart beat detector 230 operative to provide heart beat data 225 to the heart rate data analyzer 210, a human interface input device 235, and a human interface output device 240. The heart rate data analyzer 210 may include one or more memory unit(s) 220 and one or more processor(s) 215.

In some embodiments, heart rate data analyzer 210 may be configured to receive and analyze heart beat data 225. Heart beat data 225 may be a time series of heart beat values sensed at given points in time. The heart beat data may be being received in real time or near real time from heart beat detection equipment, such as heart beat detector 230, connected to a subject. Heart beat detector 230, in some embodiments may comprise electrocardiogram equipment, which is configured to couple to a subject's body in order to detect the subject's heart beat. In some embodiments, a seizure may be identified by comparing median or average heart rate values in the windows.

In some embodiments, heart rate data analyzer 210 may be configured to analyze the heart beat data and identify one or more of an onset (beginning) and an end of a seizure event that the patient may have suffered. The functionality of heart rate data analyzer 210 may be implemented using one or more processors such as processor(s) 215 and one or more memory units coupled to the one or more processors such as memory unit(s) 220.

Heart rate data analyzer 110 of FIG. 1 and heart rate data analyzer 210 of FIG. 2 may be configured to monitor the heart rate within a certain window. In some embodiments, the window may comprise two or more windows of heart beat data. In some embodiments, a seizure onset and/or offset may be identified by determining one or more parameters based on the statistical measures of heart rate in the windows, and by comparing those parameters to seizure onset and/or seizure end thresholds, respectively.

Heart rate data analyzer 210 may also be coupled to human interface input device 235 and human interface output device 240. Human interface input device 235 may be configured to allow a user of the system to input data into the system and to generally control various options. Accordingly, human interface input device 235 may be at least one of a keyboard, a touch screen, a microphone, a video camera, etc.

Human interface output device 240 may be configured to provide information to a user of the system visually, audibly, etc. Accordingly, human interface output device 240 may be at least one of a display, one or more audio speakers, haptic feedback device, etc. In some embodiments, input device 235 and output device 240 may comprise a single physical unit. In some embodiments, heart rate data analyzer 210, input device 235, and output device 240 may comprise a single physical unit.

Figure 3:
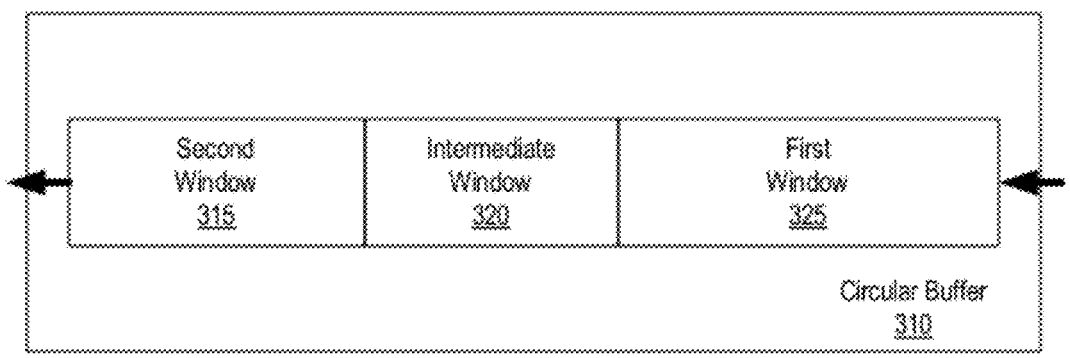
FIG. 3 is diagram illustrating an example of a circular buffer that may be used to store a moving window of heart beat data, in accordance with some embodiments.

Referring to FIG. 3, a particular embodiment of a circular buffer used to store a moving window of heart beat data is shown and generally designated 310. The circular buffer 310 may be configured to store two or more windows of heart beat data, for which computations may be performed in order to identify the onset and/or offset of an epileptic seizure. Circular buffer 310 may comprise first window 325, intermediate window 320, and second window 315. First window 325 may comprise the newest heart beat data, intermediate window 320 may comprise intermediate heart beat data, and second window 315 may comprise the oldest heart beat data.

In some embodiments, circular buffer 310 is configured to store a moving window of heart beat data versus time. Heart beat data in the circular buffer 310 shifts to the left as new heart beat data enters the right side of the circular buffer 310. As the heart rate data shifts to the left, the older data at the left side of the circular buffer 310 is overwritten, and thereby removed, at the left side of the circular buffer 310. Therefore, as newer heart beat data enters the circular buffer 310, the windows "move" to the right in time.

In some embodiments, circular buffer 310 may be configured to store two or more windows of heart beat data, for which computations may be performed in order to identify the onset and/or offset of a seizure. In some embodiments, only data from first window 325 and second window 315 may be used in the calculations while data from intermediate window 320 may be discarded as discussed here. Circular buffer 310 may be implemented similarly for either time windows, number-of-beats windows, or embodiments in which some of the windows 325, 320, and 315 are time windows and others are number-of-beats windows.

Figure 4:
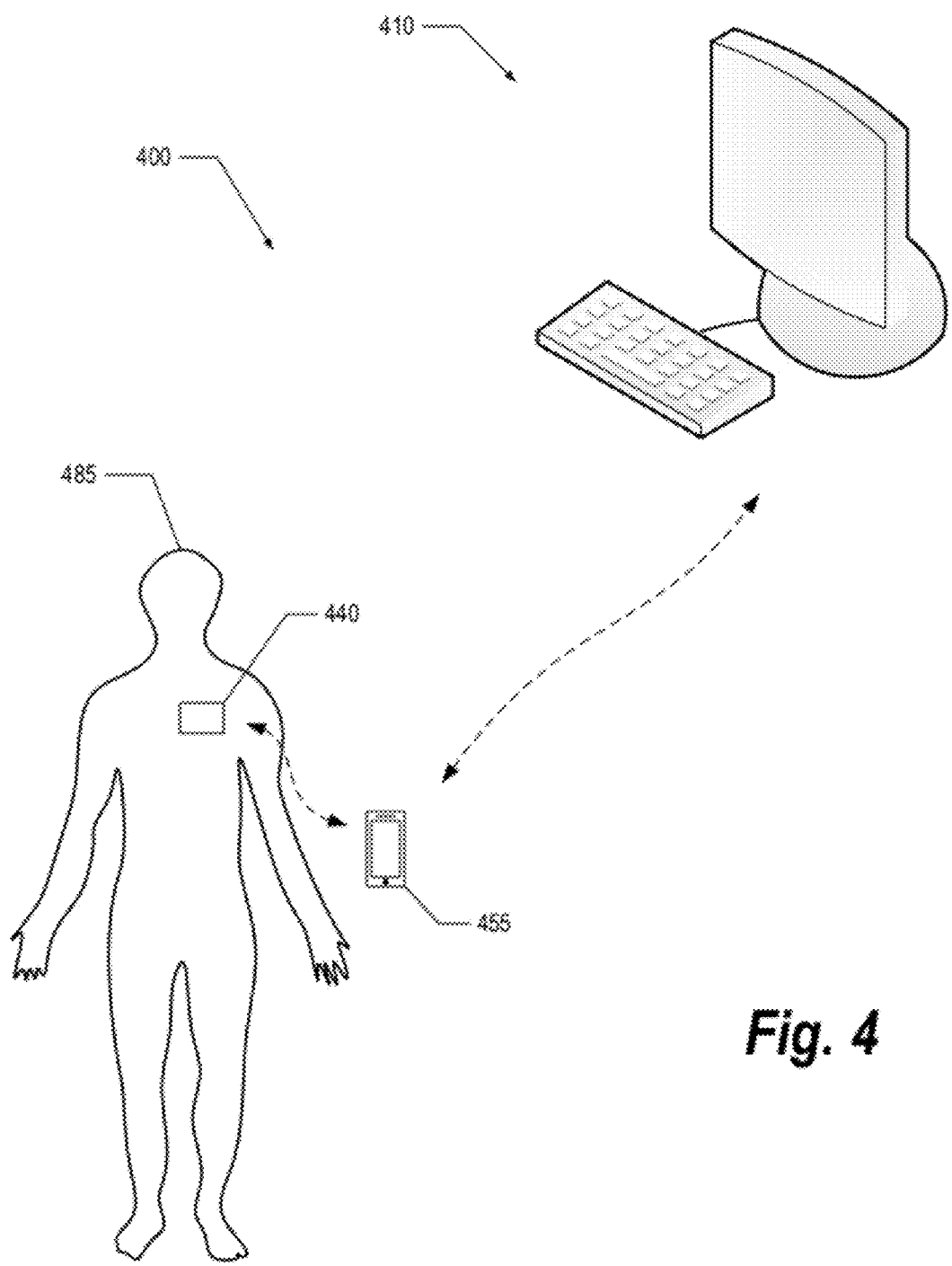
FIG. 4 is a diagram illustrating an example of obtaining heart beat data from a subject using electrocardiogram equipment, in accordance with some embodiments.

Referring to FIG. 4, a particular embodiment of a system for monitoring heart beat data from a subject is shown and generally designated 400. System 400 may include a computer 410, a heart beat sensor 440, and a controller 455.

In some embodiments, heart beat and/or heart rate data may be collected by using an external or implanted heart beat sensor and related electronics (such as heart beat sensor 440), and a controller that may be wirelessly coupled to the sensor for detecting seizure events based upon the patient's heart signal, such as controller 455. In one embodiment, sensor 440 may comprise electrodes in an externally worn patch adhesively applied to a skin surface of patient 485. The patch may include electronics for sensing and determining a heart beat signal (e.g., an ECG signal), such as an electrode, an amplifier and associated filters for processing the raw heart beat signal, an A/D converter, a digital signal processor, and in some embodiments, an RF transceiver wirelessly coupled to a separate controller unit, such as controller 455. In some embodiments, the controller unit may be part of the patch electronics.

The controller 455 may implement an algorithm for detection of seizure events based on the heart signal. It may comprise electronics and memory for performing computations of, e.g. HR parameters such as median HR values for the first and second windows, determination of ratios and/or differences of the first and second HR measures, and determination of seizure onset and offset times according to the foregoing disclosure. In some embodiments, the controller 455 may include a display and an input/output device. The controller 455 may comprise part of a handheld computer such as a PDA, a cellphone, an iPod® or iPad®, etc.

In the example shown, patch 440 may be placed on a body surface suitable for detection of heart signals. Electrical signals from the sensing electrodes may be then fed into patch electronics for filtering, amplification and A/D conversion and other preprocessing, and creation of a time-of-beat sequence (e.g., an R-R interval data stream), which may then be transmitted to controller 455. Patch 440 may be configured to perform various types of processing to the heart rate data, including filtering, determination of R-wave peaks, calculation of R-R intervals, etc. In some embodiments, the patch electronics may include the functions of controller 455, illustrated in FIG. 4 as separate from patch 440.

The time-of-beat sequence may be then provided to controller 455 for processing and determination of seizure onset and offset times and related seizure metrics. Controller 455 may be configured to communicate with computer 410. Computer 410 may be located in the same location or computer 410 may be located in a remote location from controller 455. Computer 410 may be configured to further analyze the heart data, store the data, retransmit the data, etc. Computer 410 may comprise a display for displaying information and results to one or more users as well as an input device from which input may be received by the one or more users. In some embodiments, controller 455 may be configured to perform various tasks such as calculating first and second HR measures, HR parameters, comparing HR parameters to appropriate thresholds, and determining of seizure onset and seizure end times, and other seizure metrics.

In some respects, disclosed is a computer program product embodied in a computer-operable medium, the computer program product comprising logic instructions, the logic instructions being effective to determine heart rate (HR) versus time, to determine a first HR measure for a first window, to determine a second HR measure for a second window, where at least a portion of the first window occurs after the second window. The logic instructions are further effective to determine at least one HR parameter based upon said first HR measure and said second HR measure, to identify an onset of the seizure event in response to determining that at least one HR parameter crosses an onset threshold, and to identify an end of the seizure event in response to determining that at least one HR parameter crosses an offset threshold.

Additionally, in some embodiments the first window and the second window are separated by an intermediate window. The first window, the intermediate window, and the second window may be windows in either a time domain or heart beat domain.

Additionally, the first HR measure may be a statistical measure of central tendency of heart rate in the first window (e.g., a median or average), the second HR measure may be a statistical measure of central tendency of heart rate in the second window, the at least one HR parameter may be a ratio of the first HR measure and the second HR measure, the at least one HR parameter crossing the onset threshold may comprise the HR parameter being greater than the onset threshold. In one embodiment, the onset threshold may be 1.25, and the offset threshold may be 1.1.

Additionally, the at least one HR parameter crossing the offset threshold may comprise the HR parameter being less than the offset threshold.

Additionally, the first window, the intermediate window, and the second window may be moving windows stored in a circular buffer, such as the circular buffer 310 of FIG. 3.

In some embodiments, system 400 may be configured to detect a seizure by monitoring heart beat data versus time data for a subject/patient. The subject's time of beat sequence may be obtained in real time or near real time using various methods, including well-known electrocardiogram (ECG) processes. In alternative embodiments, previously stored/recorded HR data may be provided for analysis.

It should also be noted that the heart beat data may be also received as a series of heart beats, each with a time stamp. In such embodiments, HR may be computed from the heart beat data. In some embodiments, the HR may be computed by dividing 60 by the time (in seconds) between two consecutive heart beats. In other embodiments, more advanced mathematical methods may be implemented (such as filtering, etc.) to more accurately compute HR data from heart beat data. In some embodiments, calculations may be performed using heart beat data (e.g., R-R intervals) instead of heart rate data. Although many particular embodiments hereinafter are described with calculations based on heart rate and/or heart rate parameters, similar or equivalent calculations may be performed using heart beat data and/or parameters, without determining heart rate.

In general, a seizure may cause an increase in a subject's HR during the onset of the seizure and a corresponding decrease in HR during/after the offset of a seizure. Typically, the HR may be at a resting HR before the seizure, may increase at the beginning of a seizure, rise to a certain peak HR during the seizure, and then decrease back to a resting HR after the seizure has ended. This series of HR changes associated with the seizure may be used in the seizure identification process.

Figure 5:
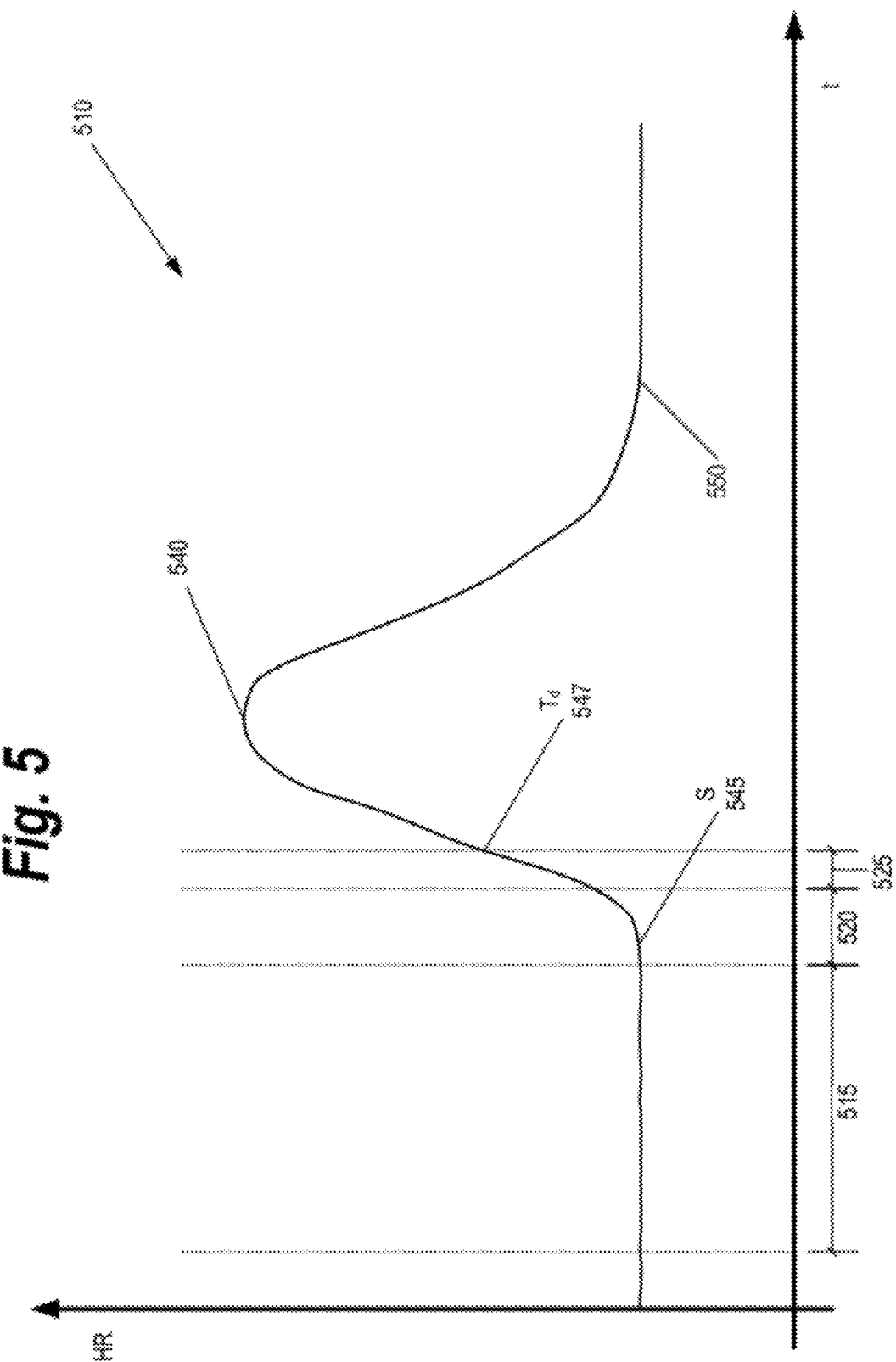
FIG. 5 is a graph of heart rate versus time illustrating an example of identifying the onset of a seizure using heart rate measures in two or three windows, in accordance with some embodiments.

Referring to FIG. 5, a particular illustrative embodiment of a graph of heart rate versus time illustrating an example of identifying the onset of a seizure using heart rate measures in two or three windows is shown and generally designated 510.

Graph 510 shows the rise of a subject's heart rate (HR) from a pre-ictal baseline HR to a peak HR (at point 540) following the onset of a seizure at time S 545. Graph 510 also shows the decrease of a subject's heart rate (HR) from peak HR 540 to a post-ictal baseline HR (at point 550) following the end of a seizure. Examples of moving time windows of HR data are also shown. In this example, the moving windows comprise first window 525, intermediate window 520, and second window 515, determined for a time Td occurring at the end of the first window, at a time when a seizure event is detected. As illustrated, window 525 comprises an immediately preceding time period relative to time Td 547, and may be referred to as a foreground time window. Time window 515, in contrast, occurs in a time period prior to window 525, and may be referred to as a background time window. Time window 520 occurs between windows 525 and 515 and may be termed an intermediate window. As time moves forward from time Td 547, the windows 525, 520, and 515 would also move forward, and HR measures determined for those windows would likewise change as the heart beats falling within the windows change.

In some embodiments, the onset of a seizure may be identified by computing and comparing heart rate measures for first window 525 and second window 515 as discussed here. The data from intermediate window 520, which may contain transient values, may be discarded.

Without being limited by theory, it is believed that providing an intermediate window allows the transitional effect of moving from a stable heart rate (second window) to an increasing heart rate (first window) to be isolated and removed. Consequently, the contrast between a relatively stable heart rate (second window) and an increasing heart rate (first window), as measured by a ratio of the windows, is detected more quickly. As shown in FIG. 5 for a point Td 547 at which a seizure is detected, the average or median heart rate for the background (second) window 515 remains low while the average or median heart rate for the foreground (first) window has risen noticeably above the background rate. Because of intermediate window 20, the value of the background (second window) heart rate does not reflect any of the increase in HR that began at point S, associated with a HR increase caused by a seizure. Thus the ratio HR1/HR2 reaches a threshold value sooner.

Figure 6:
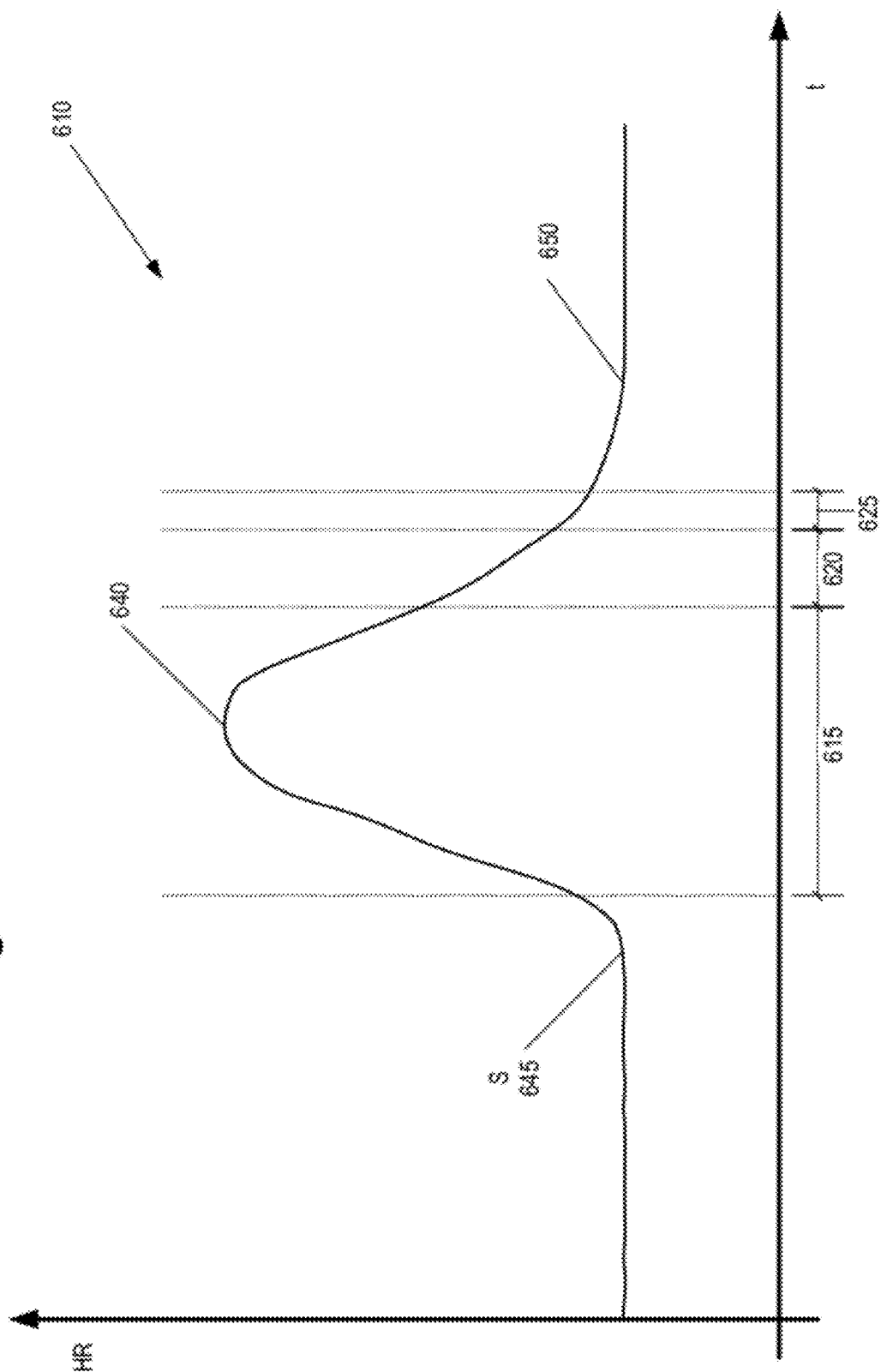
FIG. 6 is a graph of heart rate versus time illustrating an example of identifying the offset of a seizure using heart rate measures in two or three windows, in accordance with some embodiments.

Referring to FIG. 6, a particular embodiment of a graph of heart rate versus time illustrating an example of identifying the end of a seizure using heart beat data in two or three windows is shown and generally designated 610.

Graph 610 shows the rise of a subject's heart rate (HR) from a stable HR (at point S 645) to a peak HR (at point 640) following the onset of a seizure. Graph 610 also shows the decrease of a subject's heart rate (HR) from a peak HR (at point 640) to a stable HR (at point 650) following the end of a seizure. An example of a moving time window of HR data is shown. In this example, the moving window comprises first window 625, intermediate window 620, and second window 615.

In some embodiments, the offset of the seizure may be identified by computing and comparing heart rate measures for first window 625 and second window 615 as discussed here. The data from intermediate window 620, which may contain transient values, may be discarded.

Referring to FIGS. 5-6, a window of HR (or heart beat) values versus time may be processed in order to identify a seizure event. The window may be a moving window in time, and in some embodiments, the window may be a moving window in real time in order to provide real time or near real time detection of seizures. In some embodiments, the moving window may be a number-of-beats window instead of a time window. The window may be implemented using the circular buffer 310 of FIG. 3. In some embodiments, newer values may enter the buffer on one side as older values are deleted from the buffer on the other side. In some embodiments, the circular buffer 310 may be implemented using one or more pointers to indicate the memory location of the buffer "sides", such that newer values simply overwrite the older values while the side pointer(s) point to a new location.

In some embodiments, the time window may comprise two time/heart beat windows: a first window and a second window, where at least a portion of the first window occurs after the second window. The first window may have a chosen first time/heart beat width, and the second window may have a chosen second time/heart beat width. The first and second widths may be each chosen in such a way as to optimize the identification of seizures. For example, the widths may be chosen by maximizing the accuracy of the identification process using binary statistics.

In some embodiments, a first HR measure may be computed for the first window, a second HR measure may be computed for the second window, and at least one HR parameter may be determined based on the first HR measure and the second HR measure. A seizure onset may then be identified in response to determining that at least one HR parameter crosses an onset threshold. Similarly, a seizure offset may be identified in response to determining that at least one HR parameter crosses an offset threshold.

In some embodiments, the first HR measure may be a first statistical measure of central tendency of HR in the first window, and the second HR measure may be a second statistical measure of central tendency of HR in the second window. In some embodiments, the first HR measure and the second HR measure may be computed using various averaging methods such the mean, the median, Gaussian-weighted values centered around a point in the window, etc.

In some embodiments, at least one of the HR parameters may be a ratio of the first HR measure to the second HR measure. In alternative embodiments, at least one of the HR parameters may be a difference between the first HR measure and the second HR measure. A seizure onset may be then identified in response to determining that the HR parameter is greater than an onset threshold value. Similarly, a seizure offset (the end of the seizure) may be identified in response to determining that the HR parameter is less than an offset threshold value.

In some embodiments, at least one of the HR parameters may be a duration of another HR parameter exceeding a threshold value. For example, a seizure onset may be identified only when a ratio of the first HR measure and the second HR measure exceeds a threshold value for at least a defined time period, such as 5, 10, or 15 seconds. Such a duration constraint threshold could be used to avoid a false positive detection when the patient undergoes a brief period of HR elevation such as standing from a sitting or reclined position, or climbing a flight of stairs.

In some embodiments, the first HR measure may be a first standard deviation of HR in the first window, and the second HR measure may be a second standard deviation of HR in the second window. In some embodiments, at least one of the HR parameters may be the difference between the first standard deviation HR and the second standard deviation HR. In some embodiments, at least one of the HR parameters may be a ratio of the first standard deviation and the second standard deviation. A seizure onset or offset may be then identified (or in some embodiments, the seizure identification may be confirmed) in response to determining that the HR parameter is greater than an onset or offset threshold value.

In some embodiments, a seizure detection (i.e., the detection of a seizure onset) may be additionally confirmed by determining that the end of the seizure occurs within a certain time range from the seizure detection or onset. Accordingly, by restricting the time range within which the offset of a seizure may occur after the onset of the seizure to typical time ranges for a seizure, events with time ranges between detection of seizure onset and detection of seizure end that do not fall within typical or known time ranges of seizures may be rejected as seizures. In some embodiments, the time ranges may be patient-specific, i.e., determined from historical data for the patient's own seizures, while in other embodiments the ranges may be based upon aggregate data for particular patient populations. In alternative embodiments, events falling outside seizure duration ranges may be classified as other (non-seizure) events based on factors such as the magnitude, duration and trajectory of the rise and fall of the patient's heart rate. For example, events with a time range of less than 5 seconds and greater than 10 minutes may be rejected as seizures in some embodiments. In some embodiments, other data (e.g., a triaxial accelerometer) may be used to confirm or reject seizures in conjunction with the foregoing time ranges between seizure onset and seizure end.

In some embodiments, an intermediate window may be introduced between the first and second windows. In some embodiments, HR values in the intermediate window may be discarded and not used in either the first or the second window calculations. The intermediate window may be introduced in order to discard transient values that may occur between the first window, in which HR may have already increased, and the second window, where the HR may be substantially at a stable value. By discarding transient values in the intermediate window, the ability to distinguish between a relatively stable HR and an increasing HR based on the first and second HR measures is increased.

In embodiments where moving windows are used, as the windows move, new HR measures (and thus HR parameters) may be computed for each set of windows and the seizure (onset and/or offset) identification test may be applied repeatedly.

In one exemplary embodiment, a circular buffer of a window of 50 heart beats or samples may be used. The first window may be assigned 9 samples, the intermediate window may be assigned 14 samples, and the second window may be assigned 27 samples, for example. Accordingly, a seizure onset may be identified in response to determining that the first average HR is greater than the second average HR (in embodiments where the HR measures are average HRs for the respective windows) by 25%, or equivalently that the ratio of the first HR measure to the second HR measure exceeds 1.25. Similarly, a seizure offset may be identified in response to determining that the first average HR is smaller than the second average HR (in embodiments where the HR measures are average HRs); i.e., the ratio of the first HR measure and the second HR measure falls below 1 after initially rising above a threshold exceeding 1. In one embodiment, the detection may occur when the first average HR is more than 10% smaller than the second average HR, or equivalently that the ratio of the first HR measure to the second HR measure is less than about 0.9.

In another embodiment, a moving time window may be used such that the beats within a short-term window (for example 10 seconds) may be used to determine a median HR based on all of the beats within that window. Since the window is a time window, the number of beats used in determining the median HR may vary. An intermediate time window may also be proposed in which beats occurring in that window are ignored. This window would typically be a relatively short time window, such as 5-10 seconds, although shorter or longer intermediate windows are permissible. Lastly, a longer time window, for example the 300 seconds prior to the intermediate window, may define a second window for determination of a background HR based upon a statistical measure of central tendency of the beats within that window. As with the first window, the number of beats would not be fixed.

It should also be noted that, in some embodiments, the invention may be implemented using a time-of-beat sequence for a patient's heart. In such embodiments, a sequence of times is provided at which a characteristic cardiac value (such as R waves) are detected by a sensing element. It will be appreciated that HR is determined from successive R waves by determining the R-R interval (RRI) through the formula HR=60/RRI. Heart rate may be measured on an instantaneous basis using only the two immediately preceding R waves, although such calculations are frequently characterized by significant variations relating to the natural heart rate variability (HRV) associated with the respiratory and other systems. For this reason, median or moving average HR values may be used over longer time frames, such as 5 seconds, 10 seconds or 30 seconds, to "smooth" the HR and provide a more meaningful indication of patient status.

Figure 7:
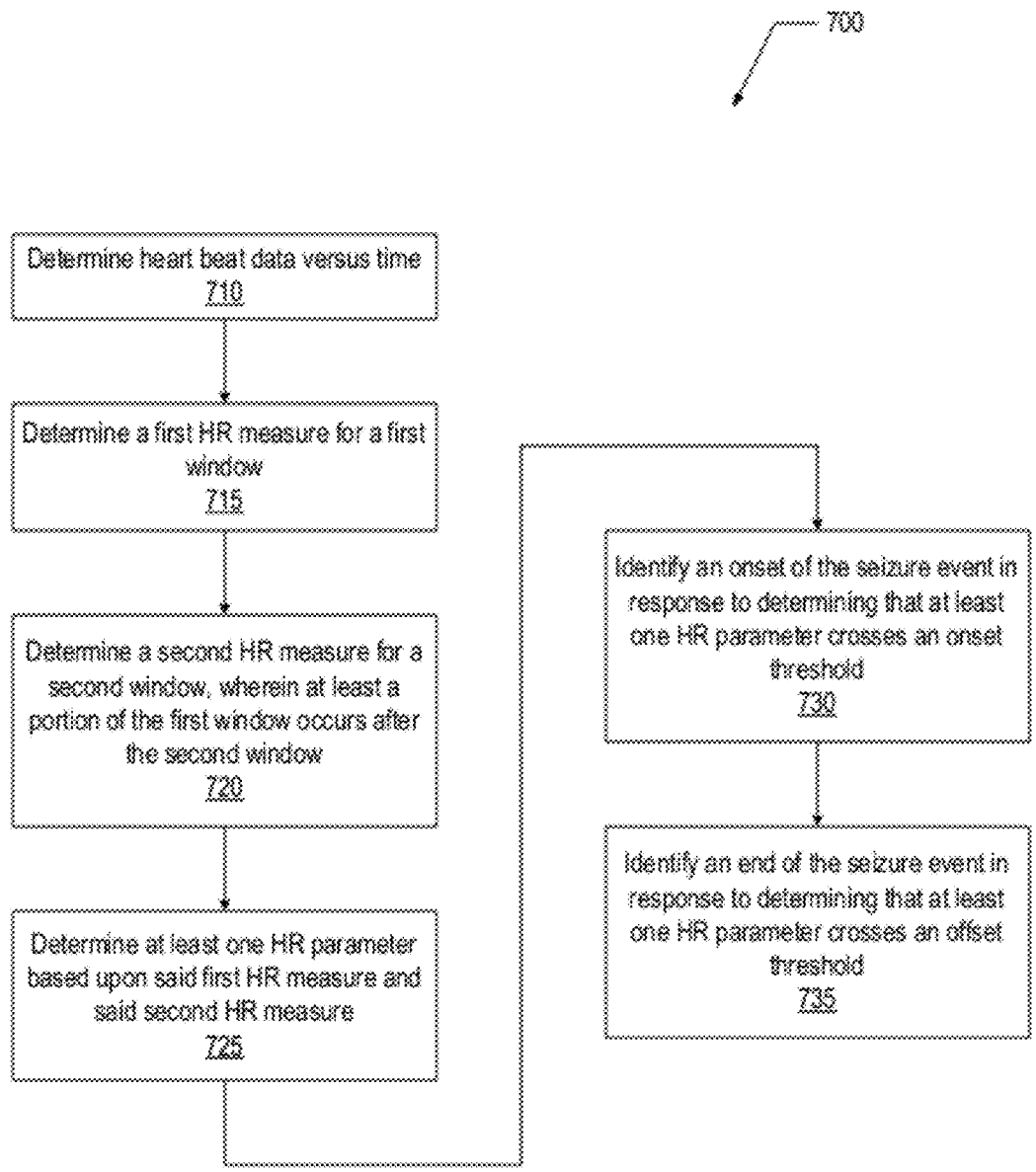
FIG. 7 is a flow diagram illustrating a method for identifying a seizure onset and an end of the seizure using heart rate data, in accordance with some embodiments.

Referring to FIG. 7, a particular embodiment of a flow diagram illustrating a method for identifying a seizure onset and a seizure end using heart rate data is shown and generally designated 700.

In some embodiments, the method illustrated in this figure may be performed by one or more of the systems illustrated in FIGS. 1-3.

At block 710 of method 700, heart beat data versus time is determined. In some embodiments, the data may be provided in real time or near real time or the data may be previously stored data that may be retrieved from storage.

At block 715, a first HR measure for a first window is determined, and at block 720, a second HR measure for a second window is determined, where at least a portion of the first window occurs after the second window.

At block 725, at least one HR parameter based upon said first HR measure and said second HR measure is determined. In one nonlimiting example, one of the HR parameters may be a ratio of the first and second HR measures. In another nonlimiting example, the difference between the first HR measure and the second HR measure may also be used as a HR parameter At block 730, an onset of the seizure event may be identified in response to determining that at least one HR parameter crosses an onset threshold. At block 735, an end of the seizure event may be identified in response to determining that at least one HR parameter crosses an offset threshold. In one nonlimiting example, a seizure onset may be identified when the ratio of the first and second HR measures exceeds 1.25, and the seizure end may be identified when the ratio falls below a threshold of about 1.0 (about 0.9, for example). In another example, an end of a seizure may be detected when the first HR value reaches a peak value and begins to decline, or declines by more than a threshold percentage or a threshold bpm magnitude. Other HR parameters may be used to determine seizure onset and end. For example, duration constraints may also be required, such that the seizure onset and offset may not be declared unless the onset or offset threshold is exceeded for 5 consecutive seconds. For example, the end of a seizure may be declared when the ratio of the first and second threshold falls below 1.0 and remains below 1.0 for 10 consecutive seconds, or alternatively that the first HR value declines for 10 consecutive seconds.

Additionally, the method 700 may further comprise an intermediate window separating the first window and the second window. The first window, the intermediate window, and the second window may be windows in either a time domain or heart beat domain. Additionally, the first window, the intermediate window, and the second window may be moving windows stored in a circular buffer.

Additionally, the first HR measure may be a statistical measure of central tendency of heart rate in the first window (e.g., a median or average), the second HR measure may be a statistical measure of central tendency of heart rate in the second window, at least one HR parameter may be a ratio of the first HR measure and the second HR measure, identifying an onset of the seizure event may comprise the HR parameter being greater than the onset threshold, and identifying the end of the seizure event may comprise the HR parameter being less than the offset threshold.

Figure 8:
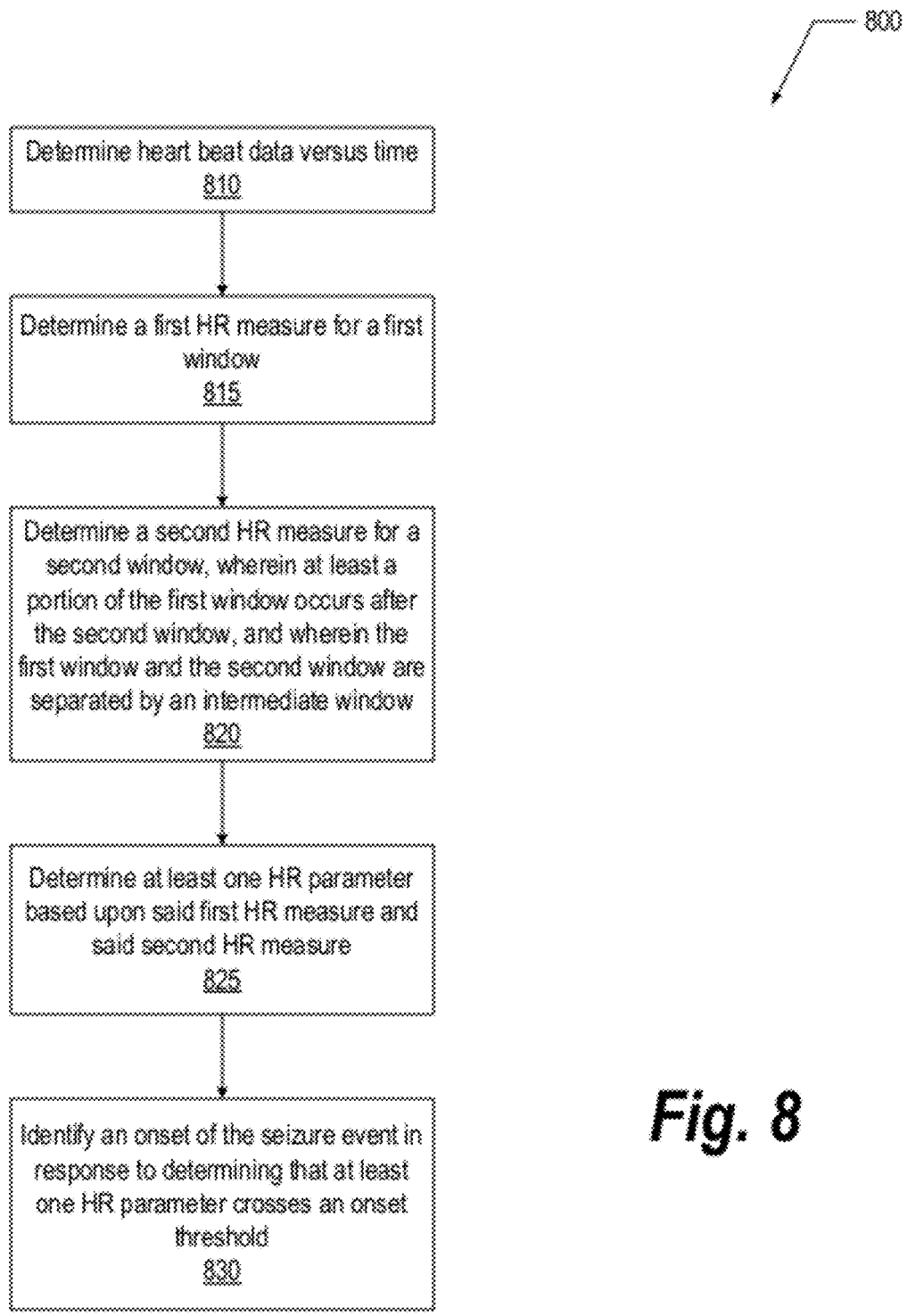
FIG. 8 is a flow diagram illustrating a method for identifying a seizure onset and an end of the seizure using heart rate data using an intermediate window, in accordance with some embodiments.

Referring to FIG. 8, a particular illustrative embodiment of a flow diagram illustrating a method for identifying a seizure using heart rate data is shown and generally designated 800. In some embodiments, the method illustrated in this figure may be performed by one or more of the systems illustrated in FIGS. 1-3.

At block 810 of method 800, heart beat data versus time is determined. In some embodiments, the data may be provided in real time or near real time or the data may be previously stored data that may be retrieved from storage.

At block 815, a first HR measure for a first window is determined, and at block 820, a second HR measure for a second window is determined, where at least a portion of the first window occurs after the second window, and where the first window and the second window are separated by an intermediate window such that at least a portion of the intermediate window occurs after the second window and before the first window.

At block 825, at least one HR parameter is determined based upon said first HR measure and said second HR measure.

At block 830, an onset of the seizure event is identified in response to determining that at least one HR parameter crosses an onset threshold.

Additionally, the method 800 may further comprise identifying an end of the seizure event in response to determining that at least one HR parameter crosses an offset threshold.

Figure 9:
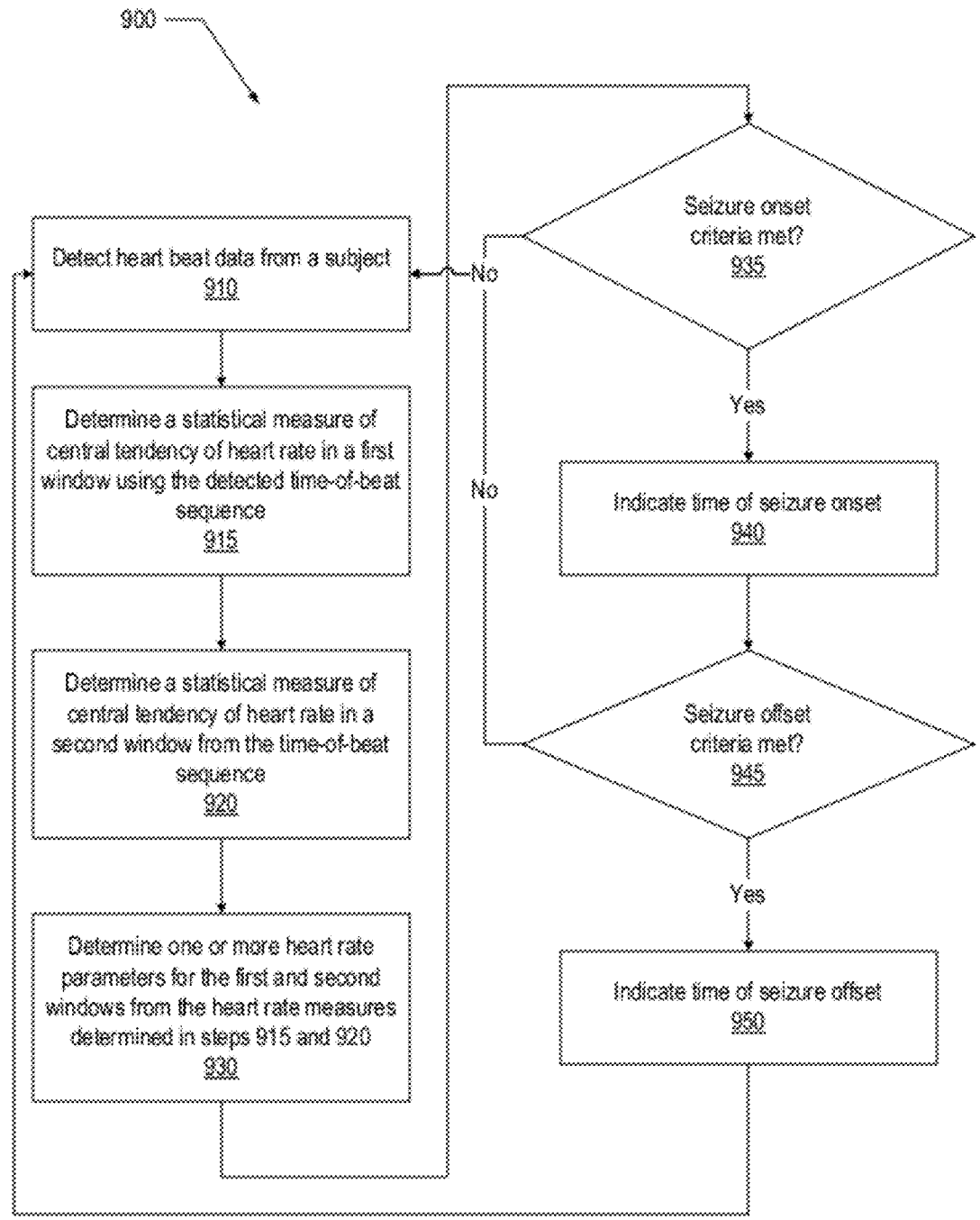
FIG. 9 is a flow diagram illustrating an alternative method for identifying a seizure onset and an end of the seizure using heart rate data, in accordance with some embodiments.

Referring to FIG. 9, a particular illustrative embodiment of a flow diagram illustrating a method for identifying a seizure using heart rate data is shown and generally designated 900.

In some embodiments, the method illustrated in this figure may be performed by one or more of the systems illustrated in FIGS. 1-3.

At block 910, heart beat from a subject is detected. In some embodiments, an electrocardiogram may be used to detect an R-wave sequence and determine a time-of-beat sequence of a heart beat of the patient.

At block 915, a statistical measure of central tendency of heart rate in a first window is determined using the detected time-of-beat sequence. The statistical measure may be determined for R-R intervals rather than heart rate; the R-waves in the R-wave sequence need not be mathematically transformed into heart rate using the formula HR=60/(R-R interval). Other heart rate measures for the first window. For example standard deviation of heart rate, may also be determined.

At block 920, a statistical measure of central tendency of heart rate in a second window is determined from the time-of-beat sequence, where the first window and the second window are separated by an intermediate window such that at least a portion of the intermediate window occurs after the second window and before the first window. Other heart rate measures for the second window, for example standard deviation of heart rate, may also be determined.

At block 930, one or more heart rate parameters may be determined for the first and second windows from the heart rate measures determined in steps 915 and 920. The heart rate parameters may include, for example, a ratio of the statistical measures of central tendency of heart rate in the first and second windows; a difference between the statistical measure of central tendency of heart rate in the first and second windows; a difference between the first standard deviation of heart rate in the first window and the second window; and a ratio of the standard deviations of heart rate in the first and second windows.

At decision 935, a determination is made as to whether at least one of one or more seizure detection criteria is met. In one embodiment, the detection criteria may include one or more of: 1) whether the ratio of the statistical measure of central tendency of heart rate for the first window to the statistical measure of central tendency of heart rate for the second window is greater than an onset threshold ratio (e.g., 1.25); and 2) whether the difference between the statistical measure of central tendency of heart rate for the first window minus the statistical measure of central tendency of heart rate for the second window exceeds a first difference threshold. In some embodiments, the detection criteria may also include one or more of: whether the first standard deviation is less than the second standard deviation; and whether the ratio of the first standard deviation to the second standard deviation is less than a threshold (e.g., 0.9). If the detection criteria of decision 935 is/are false, decision 935 branches to the "no" branch and processing continues at block 910, where new data is processed.

On the other hand, if the condition(s) of decision 935 is/are true, decision 935 branches to the "yes" branch where, at block 940, the time at which the decision criteria became true (e.g., a timestamp) is indicated as a seizure onset time. In some embodiments, a detection (i.e., seizure onset) flag is set. In some embodiments, setting the detection flag indicates that a seizure onset has been detected, a fact that will be used later during the processing.

At decision 945, a determination is made as to whether at least one of one or more seizure end decision criteria is met. In one embodiment, the seizure end criteria may include one or more of: 1) whether the ratio of the statistical measure of central tendency of heart rate in the first window to the statistical measure of central tendency in the second window is below an offset threshold (e.g. 0.9); 2) whether an absolute value of a difference between the statistical measure of central tendency of heart rate in the first window and the statistical measure of central tendency of heart rate in the second window is above an offset difference threshold (e.g., 10 bpm); and 3) whether the detection flag is set. If the condition(s) of decision 945 is false, decision 945 branches to the "no" branch and processing continues at block 910, where new data is processed.

On the other hand, if the condition(s) of decision 945 is true, decision 945 branches to the "yes" branch where, at block 950, the time at which the offset criteria became true is indicated as a seizure end time, and in embodiments the detection (i.e., seizure onset) flag is reset and/or cleared, or a seizure end flag may be set. Appropriate determination and logging of statistical and other measures of the seizure event (e.g., onset and offset time, duration, magnitude of HR increase/decrease, etc.) may also be determined.

Processing subsequently returns to block 910, where new data is processed.

In some respects, disclosed is a method for characterizing a seizure event in a patient, the method comprising determining heart rate (HR) versus time, determining a first HR measure for a first window, determining a second HR measure for a second window, wherein the first window occurs after the second window, and wherein the first window and the second window are separated by an intermediate window, determining at least one HR parameter based upon said first HR measure and said second HR measure, identifying an onset of the seizure event in response to determining that at least one HR parameter crosses an onset threshold and crosses a seizure end threshold after crossing the onset threshold.

In some respects, disclosed is a system for characterizing a seizure event in a patient, the system comprising one or more processors, one or more memory units coupled to the one or more processors, the system being configured to determine a time of beat sequence of the patient's heart, determine a first HR measure for a first window, determine a second HR measure for a second window, wherein at least a portion of the first window occurs after the second window, determine at least one HR parameter based upon the first HR measure and the second HR measure, identify a seizure event in response to determining 1) that at least a first HR parameter crosses an onset threshold, and 2) that at least a second HR parameter crosses a seizure end threshold after the first HR parameter crosses the onset threshold.

Additionally, the first window and the second window may be separated by an intermediate window. The first window, the intermediate window, and the second window may be windows in either a time domain or a heart beat domain.

Additionally, the first HR measure may be a first median HR in the first window, the second HR measure may be a second median HR in the second window, a first and second HR parameter may be a ratio of the first median HR to the second median HR, the at least a first HR parameter crossing the onset threshold may comprise the ratio of the first median HR to the second median HR being greater than the onset threshold, and the at least a second HR parameter crossing the seizure end threshold may comprise the ratio of the first median HR to the second median HR being less than the offset threshold. In one embodiment, the onset threshold may be 1.25, and the offset threshold may be 1.0.

In some respects, disclosed is a system for characterizing a seizure event in a patient, the system comprising one or more processors, one or more memory units coupled to the one or more processors, the system being configured to determine a time of beat sequence of the patient's heart, determine a first HR measure for a first window, determine a second HR measure for a second window, wherein the first window occurs after the second window, and wherein the first window and the second window are separated by an intermediate window, determine at least one HR parameter based upon the first HR measure and the second HR measure, identify a seizure event in response to determining that at least one HR parameter crosses an onset threshold.

Additionally, the system may be further configured to identify an end of the seizure event in response to determining that at least one HR parameter crosses a seizure end threshold.

In some respects, disclosed is a computer program product embodied in a computer-operable medium, the computer program product comprising logic instructions, the logic instructions being effective to determine a time of beat sequence of the patient's heart, determine a first HR measure for a first window, determine a second HR measure for a second window, wherein at least a portion of the first window occurs after the second window, determine at least one HR parameter based upon the first HR measure and the second HR measure, and identify a seizure event in response to determining 1) that at least a first HR parameter crosses an onset threshold, and 2) that at least a second HR parameter crosses an end of seizure threshold after the first HR parameter crosses the onset threshold.

Additionally, in some embodiments the first window and the second window are separated by an intermediate window. The first window, the intermediate window, and the second window may be time windows or number-of-beat windows.

In some respects, disclosed is a computer program product embodied in a computer-operable medium, the computer program product comprising logic instructions, the logic instructions being effective to determine a time of beat sequence of the patient's heart, determine a first HR measure for a first window, determine a second HR measure for a second window, wherein the first window occurs after the second window, and wherein the first window and the second window are separated by an intermediate window, determine at least one HR parameter based upon the first HR measure and the second HR measure, and identify a seizure event in response to determining that at least one HR parameter crosses an onset threshold.

Additionally, the instructions may be further effective to identify an end of the seizure event in response to determining that at least one HR parameter crosses a seizure end threshold.

In many embodiments previously discussed, identification of seizures is disclosed in terms of "heart rate measures" or "heart rate parameters." In some embodiments, calculations may be performed using heart beat data (e.g., R-R intervals) instead of heart rate data. Calculations performed for seizure detection may be made using either heart rate data or heart beat data. Thus, in embodiments involving calculations of "heart rate" measures and/or parameters, similar or equivalent calculations may be performed using heart beat data, without determining heart rate. "HR measure" may refer to an instantaneous HR or may refer to a statistical measure of central tendency (e.g., a median or an average/mean) in a window (e.g., a time window or a number-of-beats window).

"HR measure" may refer to an instantaneous HR or may refer to a statistical measure of central tendency (e.g., a median or an average/mean) in a window (e.g., a time window or a number-of-beats window). Parameters such as differences and/or ratios of short and long windows may be used to provide meaningful indications of changes in the cardiac status of a patient. Additional parameters, such as duration constraints, may also be imposed to minimize false positive and/or negative seizure detections. Duration constraints may require, for example, that threshold crossings be maintained for a defined duration or longer, or must occur for a defined duration or less.

The previous description of the disclosed embodiments is provided to enable persons skilled in the art to make or use the present claimed subject matter. Various modifications to these embodiments will be readily apparent to those skilled in the art, and the claimed subject matter is not intended to be limited to the embodiments shown herein but is to be accorded the widest scope consistent with the principles and novel features disclosed herein.

The benefits and advantages that may be provided by the present claimed subject matter have been described above with regard to specific embodiments. These benefits and advantages, and any elements or limitations that may cause them to occur or to become more pronounced are not to be construed as critical, required, or essential features of any or all of the claims. As used here, the terms "comprises," "comprising," or any other variations thereof, are intended to be interpreted as non-exclusively including the elements or limitations which follow those terms. Accordingly, a system, method, or other embodiment that comprises a set of elements is not limited to only those elements and may include other elements not expressly listed or inherent to the claimed embodiment.

While the present claimed subject matter has been described with reference to particular embodiments, it should be understood that the embodiments are illustrative and that the scope of the claimed subject matter is not limited to these embodiments. Many variations, modifications, additions and improvements to the embodiments described above are possible. It is contemplated that these variations, modifications, additions and improvements fall within the scope of the present disclosure as detailed within the following claims.

What is claimed is:

1. A method for characterizing a seizure event of a patient, the method comprising:
  receiving, at an analyzer device, first data during a first time period, the first data corresponding to a first beat sequence of a heart of the patient;
  determining, via the analyzer device, a first heart rate (HR) measure for a first window of the first time period based on the first data;
  determining, via the analyzer device, a second HR measure for a second window of the first time period based on the first data, wherein the first window of the first time period occurs after the second window of the first time period, and wherein an intermediate window of the first time period spans from an end of the second window to a start of the first window; and
  determining, via the analyzer device, whether an onset of the seizure event has occurred based on a ratio of the first HR measure to the second HR measure, a ratio of the second HR measure to the first HR measure, or both, wherein the analyzer device determines the onset of the seizure event without requiring brain activity data to verify the heart rate data.

2. The method of claim 1, wherein the first window of the first time period, the intermediate window of the first time period, and the second window of the first time period are consecutive time windows.

3. The method of claim 1, wherein the first HR measure is a measure of a standard deviation of HR in the first window of the first time period and wherein the second HR measure is a measure of a standard deviation of HR in the second window of the first time period.

4. The method of claim 1, further comprising:
  identifying an end of the seizure event; and
  sending information indicative of the end of the seizure event to an output device.

5. The method of claim 1, wherein the first window comprises a shorter duration than the intermediate window, and wherein the intermediate window comprises a shorter duration than the second window.

6. The method of claim 1, further comprising:
  identifying the second heart rate measure based on the second window, wherein the second heart rate measure comprises a stable heart rate;
  identifying the first heart rate measure based on the first window, wherein the first heart rate measure comprises an increasing heart rate; and
  isolating a transitional effect, the transitional effect comprises a duration, wherein the stable heart rate transitions to the increasing heart rate.

7. The method of claim 1, wherein at least the first window of the first time period of the second window of the first time period are sliding windows, and further comprising identifying, via the analyzer device, the onset of the seizure event based on a first window of a second time period and a second window of the second time period.

8. The method of claim 7, wherein the second time period at least partially overlaps the first time period.

9. The method of claim 7, wherein the second window of the second time period at least partially overlaps the first window of the first time period.

10. The method of claim 1, wherein the first window of the first time period and the second window of the first time period are sliding windows, and further comprising:
  receiving, at the analyzer device, second data corresponding to a second beat sequence of the heart of the patient during a second time period;
  determining, via the analyzer device, a third HR measure for a first window of the second time period based on the second data;
  determining, via the analyzer device, a fourth HR measure for a second window of the second time period based on the second data, wherein the first window of the second time period occurs after the second window of the second time period; and
  identifying, via the analyzer device, the onset of the seizure event in response to determining that a second ratio based on the third HR measure and the fourth HR measure, or both, exceed an onset threshold.

11. A system for identifying seizures, the system comprising:
  one or more processors; and
  one or more memory units coupled to the one or more processors, wherein the one or more memory units comprise instructions executable by the one or more processors to:
    receive data corresponding to a beat sequence of a heart of a patient during a time period;
    determine a first heart rate (HR) measure for a first window of the time period based on the data;
    determine a second HR measure for a second window of the time period based on the data, wherein the first window occurs after the second window, and wherein an intermediate window of the time period spans from an end of the second window to a start of the first window;
    identify an onset of a seizure event in response to a determination that one of a ratio of the first HR measure to the second HR measure or a ratio of the second HR measure to the first HR measure satisfies an onset threshold associated with the onset of the seizure event, wherein the one or more processors determines the onset of the seizure event without requiring brain activity data to verify the heart rate data; and
    identify an end of the seizure event.

12. The system of claim 11, wherein the instructions are executable by the one or more processors to:
  determine a duration of time between the onset of the seizure event and the end of the seizure event;
  compare the duration of time to a threshold; and
  send an output to at least one output device in response to a determination that the duration of time satisfies the threshold, the output includes an indication that a seizure is detected.

13. The system of claim 11, wherein the first HR measure is one of a measure of a mean heart rate in the first window or a median heart rate in the first window, and wherein the second HR measure is one of a measure of a mean heart rate in the second window or a median heart rate in the second window.

14. A non-transitory computer-readable medium comprising instructions executable by a processor to:
- determine a first heart rate (HR) measure for a first window of a time period based on data, wherein the data corresponds to a beat sequence of a heart of a patient during the time period;
- determine a second HR measure for a second window of the time period based on the data, wherein the first window occurs after the second window, and wherein an intermediate window of the time period spans from an end of the second window to a start of the first window;
- determine a ratio based on the first HR measure and the second HR measure;
- identify an onset of a seizure event in response to a determination that the ratio satisfies an onset threshold, wherein the processor determines the onset of the seizure event without requiring brain activity data to verify the heart rate data; and
- send information indicative of the onset of the seizure event to an output device.

15. The non-transitory computer-readable medium of claim 14, where the first window, the intermediate window, and the second window are time windows or number-of-beats windows.

16. The non-transitory computer-readable medium of claim 14, wherein the first HR measure comprises a statistical measure of central tendency of HR in the first window, and wherein the second HR measure comprises a statistical measure of central tendency of HR in the second window.

17. The non-transitory computer-readable medium of claim 16, wherein the statistical measure of the central tendency of HR in the first window includes one of a mean heart rate in the first window and a standard deviation of HR in the first window, and wherein the statistical measure of the central tendency of HR in the second window includes one of a mean heart rate in the second window or a standard deviation of HR in the second window.

18. The non-transitory computer-readable medium of claim 14, wherein the instructions are further executable by the processor to identify an end of the seizure event.

19. The non-transitory computer-readable medium of claim 14, wherein the ratio comprises a first ratio of the first HR measure to the second HR measure.

20. The non-transitory computer-readable medium of claim 14, wherein the ratio comprises a second ratio of the second HR measure to the first HR measure.

* * * * *